US006306659B1

(12) United States Patent
Parce et al.

(10) Patent No.: US 6,306,659 B1
(45) Date of Patent: Oct. 23, 2001

(54) HIGH THROUGHPUT SCREENING ASSAY SYSTEMS IN MICROSCALE FLUIDIC DEVICES

(75) Inventors: J. Wallace Parce, Palo Alto; Anne R. Kopf-Sill, Portola Valley; Luc J. Bousse, Menlo Park, all of CA (US)

(73) Assignee: Caliper Technologies Corp., Mountain View, CA (US)

( * ) Notice: Subject to any disclaimer, the term of this patent is extended or adjusted under 35 U.S.C. 154(b) by 0 days.

(21) Appl. No.: 09/196,535

(22) Filed: Nov. 20, 1998

Related U.S. Application Data

(63) Continuation of application No. 08/881,696, filed on Jun. 24, 1997, which is a continuation-in-part of application No. 08/761,575, filed on Dec. 6, 1996, now Pat. No. 6,046,056, and a continuation-in-part of application No. 08/671,987, filed on Jun. 28, 1996, now Pat. No. 5,942,443.

(51) Int. Cl.$^7$ ........................... G01N 35/02; G01N 21/00
(52) U.S. Cl. ........................... 436/47; 436/514; 436/518; 435/4; 435/6; 435/287.3; 435/287.1; 422/55; 422/58; 422/63; 422/65
(58) Field of Search ........................... 436/47, 518, 514; 435/4, 164, 6, 810, 287.3; 422/55, 58, 102, 63, 65

(56) References Cited

U.S. PATENT DOCUMENTS

| 4,675,300 | 6/1987 | Zare et al. ........................... 436/172 |
|---|---|---|
| 4,737,464 | 4/1988 | McConnell et al. ........................... 436/43 |
| 4,740,708 | * 4/1988 | Batchelder . |
| 4,908,112 | 3/1990 | Pace ........................... 204/299 R |
| 4,963,498 | 10/1990 | Hillman et al. ........................... 436/69 |

(List continued on next page.)

FOREIGN PATENT DOCUMENTS

| 568902 | 11/1993 | (EP) | ........................... F04B/43/04 |
|---|---|---|---|
| 637998 | 7/1996 | (EP) | ........................... B01L/3/00 |
| 639223 | 7/1996 | (EP) | ........................... C12M/3/00 |
| 2248891 | 4/1992 | (GB) | ........................... F04B/21/00 |
| WO94/05414 | 3/1994 | (WO) . | |

(List continued on next page.)

OTHER PUBLICATIONS

Weaver et al. (Sep. 1998) "Gel microdroplets: Rapid detection & enumeration of individual microorganisms by their metabolic activity," *Bio/Technology* 6:1084–1089.

Manz et al. (1990) "Miniaturized Total Chemical Analysis Systems: A Novel Concept for Chemical Sensing," *Sensors and Actuators* B1:244–248.

Manz et al. (1991) "Micromachining of Monocrystalline Silicon and Glass for Chemical Analysis Systems," *Trends in Analytical Chemistry* 10(5):144–149.

Linhares and Kissinger (1991) "Use of an On–Column Fracture in Capillary Zone Electrophoresis for Sample Introduction," *Anal. Chem.* 63:2076–2078.

Bunin & Ellman (1992) "A General and Expedient Method for the Solid–Phase Synthesis of 1,4–Benzodiazepine Derivatives," *J. Amer. Chem.* 114:10997–10998.

(List continued on next page.)

Primary Examiner—Christopher L. Chin
Assistant Examiner—Minh-Quan K. Pham
(74) Attorney, Agent, or Firm—Jonathan Alan Quine; Matthew B. Murphy; Law Offices of Jonathan Alan Quine

(57) ABSTRACT

An apparatus for analyzing a plurality of compounds is used in conjunction with microfluidic devices for performing high throughput screening assays. A conveyor system delivers libraries of compounds to a microfluidic device which accesses the compounds in order to screen large numbers of different compounds for their effects on a variety of chemical and biochemical systems.

20 Claims, 19 Drawing Sheets

U.S. PATENT DOCUMENTS

| | | | |
|---|---|---|---|
| 4,978,503 | 12/1990 | Shanks et al. | 422/58 |
| 5,096,807 | 3/1992 | Leaback | 435/6 |
| 5,126,022 | 6/1992 | Soane et al. | 204/180.1 |
| 5,140,161 | 8/1992 | Hillman et al. | 250/341 |
| 5,144,139 | 9/1992 | Hillman et al. | 250/341 |
| 5,164,598 | 11/1992 | Hillman et al. | 250/341 |
| 5,171,132 | 12/1992 | Miyazaki et al. | 417/413 |
| 5,171,534 | 12/1992 | Smith et al. | 422/82.05 |
| 5,188,963 | 2/1993 | Stapleton | 435/299 |
| 5,192,405 | 3/1993 | Petersen et al. | 204/180.1 |
| 5,271,724 | 12/1993 | van Lintel | 417/413.2 |
| 5,277,556 | 1/1994 | van Lintel | 417/413 A |
| 5,278,048 | 1/1994 | Parce et al. | 436/29 |
| 5,296,375 | 3/1994 | Kricka et al. | 435/291 |
| 5,304,487 | 4/1994 | Wilding et al. | 435/291 |
| 5,324,591 | 6/1994 | Georger, Jr. et al. | 428/552 |
| 5,375,979 | 12/1994 | Trah | 417/52 |
| 5,384,261 | 1/1995 | Winkler et al. | 436/518 |
| 5,395,503 | 3/1995 | Parce et al. | 204/403 |
| 5,427,946 | 6/1995 | Kricka et al. | 435/291 |
| 5,429,734 | 7/1995 | Gajar | 204/299 R |
| 5,441,894 * | 8/1995 | Coleman et al. | |
| 5,445,939 | 8/1995 | Anderson | 435/7.24 |
| 5,486,335 | 1/1996 | Wilding et al. | 422/55 |
| 5,496,697 | 3/1996 | Parce et al. | 435/5 |
| 5,498,392 | 3/1996 | Wilding et al. | 422/68.1 |
| 5,571,410 | 11/1996 | Swedberg et al. | 210/198.2 |
| 5,585,069 | 12/1996 | Zanzucchi et al. | 422/100 |
| 5,593,838 | 1/1997 | Zanzucchi | 435/6 |
| 5,605,662 | 2/1997 | Heller et al. | 422/68.1 |
| 5,627,643 * | 5/1997 | Birnbaum. | |
| 5,632,876 * | 5/1997 | Zanzucchi et al. | |
| 5,637,469 | 6/1997 | Wilding et al. | 435/7.21 |
| 5,650,075 | 7/1997 | Haas | 216/97 |
| 5,658,723 | 8/1997 | Oberhardt | 435/4 |
| 5,699,157 | 12/1997 | Parce. | |
| 5,773,298 | 6/1998 | Lynggaard et al. | |
| 5,779,868 | 7/1998 | Parce et al. | |
| 5,780,754 | 7/1998 | Karlberg et al. | |
| 5,800,690 | 9/1998 | Chow et al. | |
| 5,842,787 | 12/1998 | Kopf-Sill et al. | |
| 5,852,495 | 12/1998 | Parce. | |
| 5,863,708 * | 1/1999 | Zanzucchi et al. | |
| 5,869,004 | 2/1999 | Parce et al. | |
| 5,876,675 | 3/1999 | Kennedy. | |
| 5,880,071 | 3/1999 | Parce et al. | |
| 5,882,465 | 3/1999 | McReynolds. | |
| 5,885,470 | 2/1999 | Parce et al. | |

FOREIGN PATENT DOCUMENTS

| | | | |
|---|---|---|---|
| WO95/12608 | 5/1995 | (WO) | C07K/1/04 |
| WO 95/27210 | 10/1995 | (WO). | |
| WO 95/27211 | 10/1995 | (WO). | |
| WO95/27210 | 10/1995 | (WO) | G01N/35/08 |
| WO95/27211 | 10/1995 | (WO) | G01N/35/08 |
| WO95/33846 | 12/1995 | (WO). | |
| WO96/04547 * | 2/1996 | (WO). | |
| WO96/14933 | 5/1996 | (WO) | B01L/3/00 |
| WO96/14934 | 5/1996 | (WO) | B01L/3/00 |
| WO96/15269 | 5/1996 | (WO) | C12Q/1/68 |
| WO96/15450 | 5/1996 | (WO). | |
| WO96/15576 | 5/1996 | (WO). | |
| WO97/02357 | 1/1997 | (WO). | |
| WO97/22000 | 6/1997 | (WO) | G01N/33/50 |
| WO 98/00231 | 1/1998 | (WO). | |
| WO 98/00705 | 1/1998 | (WO). | |
| WO 98/00707 | 1/1998 | (WO). | |
| WO 98/02728 | 1/1998 | (WO). | |
| WO 98/05424 | 2/1998 | (WO). | |
| WO98/05959 | 2/1998 | (WO). | |
| WO 98/22811 | 5/1998 | (WO). | |
| WO 98/45481 | 10/1998 | (WO). | |
| WO 98/45929 | 10/1998 | (WO). | |
| WO 98/46438 | 10/1998 | (WO). | |
| WO 98/49548 | 11/1998 | (WO). | |
| WO 98/55852 | 12/1998 | (WO). | |
| WO 98/56956 | 12/1998 | (WO). | |
| WO 99/00649 | 1/1999 | (WO). | |
| WO 99/10735 | 3/1999 | (WO). | |
| WO 99/12016 | 3/1999 | (WO). | |
| WO 99/16162 | 4/1999 | (WO). | |
| WO 99/19056 | 4/1999 | (WO). | |
| WO 99/19516 | 4/1999 | (WO). | |
| WO 99/29497 | 6/1999 | (WO). | |

OTHER PUBLICATIONS

Kikuchi et al. (Sep. 1992) *Microvasc. Res.* 44(2):226–240.

Bao et al. (1992) "Ultramicro Enzyme Assays in a Capillary Electrophoretic System," *J. Chromatog.* 608:217–224.

Harrison et al. (1992) "Capillary Electrophoresis and Sample Ijnection Systems Integrated on a Planar Glass Chip," *Anal. Chem.* 65:1926–1932.

Jung & Beck–Sickinger (1992) "Multiple Peptide Synthessis Methods and Their Applications," *Angew. Chem. Int. Ed. Engl.* 31(4):367–383.

Simon et al. (1992) "Peptoids: A Modular Approach to Drug Discovery," *PNAS* 89:9367–9371.

Zuckermann et al. (1992) "Efficient Method for the Preparation of Peptoids [Oligo(N–Substituted Glycines)] by Submonomer Solid–Phase Synthesis," *J. Amer. Chem. Soc.* 114:10646–10647.

Harmon et al. (1993) "Mathematical Treatment of Electrophoretically Mediated Microanalysis," *Anal. Chem.* 65:2655–2662.

Pavia et al. (1993) "The Generation of Molecular Diversity," *Bioorg. Med. Chem. Lett.* 3(3):387–396.

Seiler et al. (1993) "Planar Glass Chips for Capillary Electrophoresis: Repetitive Sample Injection, Quantitation, and Separation Efficiency," *Anal. Chem.* 65:1481–1488.

Cho et al. (1993) "An Unnatural Biopolymer," *Science* 261:1303–1305.

Wiley & Rich (1993) "Peptidomimetics Derived From Natural Products," *Med. Res. Rev.* 13:327–384.

Harrison et al. (1993) "Micromachining a Miniaturized Capillary Electrophoresis–Based Chemical Analysis System on a Chip," *Science* 261:895–897.

Song et al. (1994) *Anal. Chem.* 66:778–781.

Seller et al. (1994) *Anal. Chem.* 66:3485–3491.

Manz et al. (1994) "Electrosmotic Pumping and Electrophoretic Separations for Miniaturized Chemical Analysis Systems," *J. Michromach. Microeng.* 4:257–265.

Harmon et al. (1994) "Selectivity in Electrophoretically Mediated Microanalysis by Control of Product Detection Time," *Anal. Chem.* 66:3797–3805.

Woolley et al. (1994) "Ultra–High Speed DNA Fragment Separations Using Microfabricated Capillary Array Electrophoresis Chips," *PNAS* 91:11348–11352.

Dasgupta and Liu (1994) "Electroosmosis: A Reliable Fluid Propulsion System for Flow Injection Analysis," *Anal. Chem.* 66:1792–1798.

Jacobson et al. (1994) "Effects of Injection Schemes and Column Geometry on the Performance of Microchip Electrophoresis Devices," *Anal. Chem.* 66:1107–1113.

Jacobson et al. (1994) "High–Speed Separarations on a Microchip," *Anal. Chem.* 66:1114–1118.

Jacobson et al. (1994) "Open Channel Electrochromatography on a Microchip," *Anal. Chem.* 66:2369–2373.

Seiler et al.(1994) "Electoosmotic Pumping and Valveless Control of Fluid Flow Within a Manifold of Capillaries on a Glass Chip," *Anal. Chem.* 66:3485–3491.

Schmalzing et al. (1995) "Solution–Phase Immunoassay for Determination of Cortisol in Serum by Capillary Electrophoresis," *Clin. Chem.* 41(9):1403–1406.

Jacobson et al. (Apr. 1995) 16(4):481–486.

Ramsey et al. (1995) "Microfabricated Chemical Measurement Systems," *Nature Med.* 1(10):1093.

Jacobson et al. (1995) "Fused Quartz Substrates for Microchip Electrophoresis," *Anal. Chem.* 67(13):2059–2063.

Kounty et al. (1996) "Microchip Electrophoretic Immunoassay for Serum Cortisol," *Anal. Chem.* 68:18–22.

Chu et al. (1966) "Affinity Capillary Electrophoresis–Spectrometry for Screening Combinatorial Libraries," *J. Am. Chem. Soc.* 118:7827–7835.

* cited by examiner

HIGH THROUGHPUT SCREENING ASSAY SYSTEMS IN MICROSCALE FLUIDIC DEVICES

CROSS-REFERENCE TO RELATED APPLICATIONS

This application is a continuation of U.S. application Ser. No. 08/881,696 filed Jun. 24, 1997, which is a continuation-in-part of U.S. application Ser. No. 08/761,575 filed Dec. 6, 1996, now U.S. Pat. No. 6,046,056, and is a continuation-in-part of U.S. application Ser. No. 08/671,987, filed Jun. 28, 1996, now U.S. Pat. No. 5,942,443, each of which is hereby incorporated herein by reference in its entirety for all purposes. A PCT Application designating the United States of America, WO8/00231, published Jan. 8, 1998, substantially identical to the present application, was co-filed in the United States Receiving Office on Jun. 24, 1997. This application is also incorporated herein by reference.

FIELD OF THE INVENTION

This application relates to apparatus and assay systems for detecting molecular interactions. The apparatus comprise a substrate with one or more intersecting channels and an electroosmotic fluid movement component, or other component for moving fluid in the channels on the substrate.

BACKGROUND OF THE INVENTION

There has long been a need for the ability to rapidly assay compounds for their effects on various biological processes. For example, enzymologists have long sought better substrates, better inhibitors or better catalysts for enzymatic reactions. Similarly, in the pharmaceutical industries, attention has been focused on identifying compounds that may block, reduce, or even enhance the interactions between biological molecules. Specifically, in biological systems the interaction between a receptor and its ligand often may result, either directly or through some downstream event, in either a deleterious or beneficial effect on that system, and consequently, on a patient for whom treatment is sought. Accordingly, researchers have long sought after compounds or mixtures of compounds that can reduce, block or even enhance that interaction. Similarly, the ability to rapidly process samples for detection of biological molecules relevant to diagnostic or forensic analysis is of fundamental value for, e.g., diagnostic medicine, archaeology, anthropology, and modem criminal investigation.

Modem drug discovery is limited by the throughput of the assays that are used to screen compounds that possess these described effects. In particular, screening of a maximum number of different compounds necessitates reducing the time and labor requirements associated with each screen.

High throughput screening of collections of chemically synthesized molecules and of natural products (such as microbial fermentation broths) has thus played a central role in the search for lead compounds for the development of new pharmacological agents. The remarkable surge of interest in combinatorial chemistry and the associated technologies for generating and evaluating molecular diversity represent significant milestones in the evolution of this paradigm of drug discovery. See Pavia et al., 1993, *Bioori. Med. Chem. Lett.* 3: 387–396, incorporated herein by reference. To date, peptide chemistry has been the principle vehicle for exploring the utility of combinatorial methods in ligand identification. See Jung & Beck-Sickinger, 1992, *Angew. Chem. Int. Ed. Enzl.* 31: 367–383, incorporated herein by reference. This may be ascribed to the availability of a large and structurally diverse range of amino acid monomers, a relatively generic, high-yielding solid phase coupling chemistry and the synergy with biological approaches for generating recombinant peptide libraries. Moreover, the potent and specific biological activities of many low molecular weight peptides make these molecules attractive starting points for therapeutic drug discovery. See Hirschmann, 1991, *Angew. Chem. Int. Ed. Ensl.* 30: 1278–1301, and Wiley & Rich, 1993, *Med. Res. Rev.* 13: 327–384, each of which is incorporated herein by reference. Unfavorable pharmacodynamic properties such as poor oral bioavailability and rapid clearance in vivo have limited the more widespread development of peptidic compounds as drugs, however. This realization has recently inspired workers to extend the concepts of combinatorial organic synthesis beyond peptide chemistry to create libraries of known pharmacophores like benzodiazepines (see Bunin & Elhman, 1992, *J. Amer. Chem. Soc.* 114: 10997–10998, incorporated herein by reference) as well as polymeric molecules such as oligomeric N-substituted glycines ("peptoids") and oligocarbamates. See Simon et al., 1992, *Proc. Natl. Acad. Sci. USA* 89: 9367–9371; Zuckermann et al., 1992, *J. Amer. Chem. Soc.* 114: 10646–10647; and Cho et al., 1993, *Science* 261:1303–1305, each of which is incorporated herein by reference.

In similar developments, much as modern combinatorial chemistry has resulted in a dramatic increase in the number of test compounds that may be screened, human genome research has also uncovered large numbers of new target molecules (e.g., genes and gene products such as proteins and RNA) against which the efficacy of test compounds are screened.

Despite the improvements achieved using parallel screening methods and other technological advances, such as robotics and high throughput detection systems, current screening methods still have a number of associated problems. For example, screening large numbers of samples using existing parallel screening methods have high space requirements to accommodate the samples and equipment, e.g., robotics, etc., high costs associated with that equipment, and high reagent requirements necessary for performing the assays. Additionally, in many cases, reaction volumes must be very small to account for the small amounts of the test compounds that are available. Such small volumes compound errors associated with fluid handling and measurement, e.g., due to evaporation, small dispensing errors, or the like. Additionally, fluid handling equipment and methods have typically been unable to handle these volume ranges with any acceptable level of accuracy due in part to surface tension effects in such small volumes.

The development of systems to address these problems must consider a variety of aspects of the assay process. Such aspects include target and compound sources, test compound and target handling, specific assay requirements, and data acquisition, reduction storage and analysis. In particular, there exists a need for high throughput screening methods and associated equipment and devices that are capable of performing repeated, accurate assay screens, and operating at very small volumes.

The present invention meets these and a variety of other needs. In particular, the present invention provides novel methods and apparatuses for performing screening assays which address and provide meaningful solutions to these problems.

SUMMARY OF THE INVENTION

The present invention provides methods of screening a plurality of test compounds for an effect on a biochemical system. These methods typically utilize microfabricated substrates which have at least a first surface, and at least two intersecting channels fabricated into that first surface. At least one of the intersecting channels will have at least one cross-sectional dimension in a range from 0.1 to 500 μm. The methods involve flowing a first component of a biochemical system in a first of the at least two intersecting channels. At least a first test compound is flowed from a second channel into the first channel whereby the test compound contacts the first component of the biochemical system. An effect of the test compound on the biochemical system is then detected.

In a related aspect, the method comprises continuously flowing the first component of a biochemical system in the first channel of the at least two intersecting channels. Different test compounds are periodically introduced into the first channel from a second channel. The effect, if any, of the test compound on the biochemical system is then detected.

In an alternative aspect, the methods utilize a substrate having at least a first surface with a plurality of reaction channels fabricated into the first surface. Each of the plurality of reaction channels is fluidly connected to at least two transverse channels also fabricated in the surface. The at least first component of a biochemical system is introduced into the plurality of reaction channels, and a plurality of different test compounds is flowed through at least one of the at least two transverse channels. Further, each of the plurality of test compounds is introduced into the transverse channel in a discrete volume. Each of the plurality of different test compounds is directed into a separate reaction channel and the effect of each of the test compounds on the biochemical system is then detected.

The present invention also provides apparatuses for practicing the above methods. In one aspect, the present invention provides an apparatus for screening test compounds for an effect on a biochemical system. The device comprises a substrate having at least one surface with at least two intersecting channels fabricated into the surface. The at least two intersecting channels have at least one cross-sectional dimension in the range from about 0.1 to about 500 μm. The device also comprises a source of different test compounds fluidly connected to a first of the at least two intersecting channels, and a source of at least one component of the biochemical system fluidly connected to a second of the at least two intersecting channels. Also included are fluid direction systems for flowing the at least one component within the intersecting channels, and for introducing the different test compounds from the first to the second of the intersecting channels. The apparatus also optionally comprises a detection zone in the second channel for detecting an effect of said test compound on said biochemical system.

In preferred aspects, the apparatus of the invention includes a fluid direction system which comprises at least three electrodes, each electrode being in electrical contact with the at least two intersecting channels on a different side of an intersection formed by the at least two intersecting channels. The fluid direction system also includes a control system for concomitantly applying a variable voltage at each of the electrodes, whereby movement of the test compounds or the at least first component in the at least two intersecting channels are controlled.

In another aspect, the present invention provides an apparatus for detecting an effect of a test compound on a biochemical system, comprising a substrate having at least one surface with a plurality of reaction channels fabricated into the surface. The apparatus also has at least two transverse channels fabricated into the surface, wherein each of the plurality of reaction channels is fluidly connected to a first of the at least two transverse channels at a first point in each of the reaction channels, and fluidly connected to a second transverse channel at a second point in each of the reaction channels. The apparatus further includes a source of at least one component of the biochemical system fluidly connected to each of the reaction channels, a source of test compounds fluidly connected to the first of the transverse channels, and a fluid direction system for controlling movement of the test compound and the first component within the transverse channels and the plurality of reaction channels. As above, the apparatuses also optionally include a detection zone in the second transverse channel for detecting an effect of the test compound on the biochemical system.

BRIEF DESCRIPTION OF THE DRAWING

FIG. 2A shows a system used for screening effectors of an enzyme-substrate interaction. FIG. 2B illustrates the use of the apparatus in screening effectors of receptor-ligand interactions.

FIG. 9 shows fluorescence data from a continuous flow assay screen.

DESCRIPTION OF THE PREFERRED EMBODIMENT

I. Applications for the Invention

Figure 1:
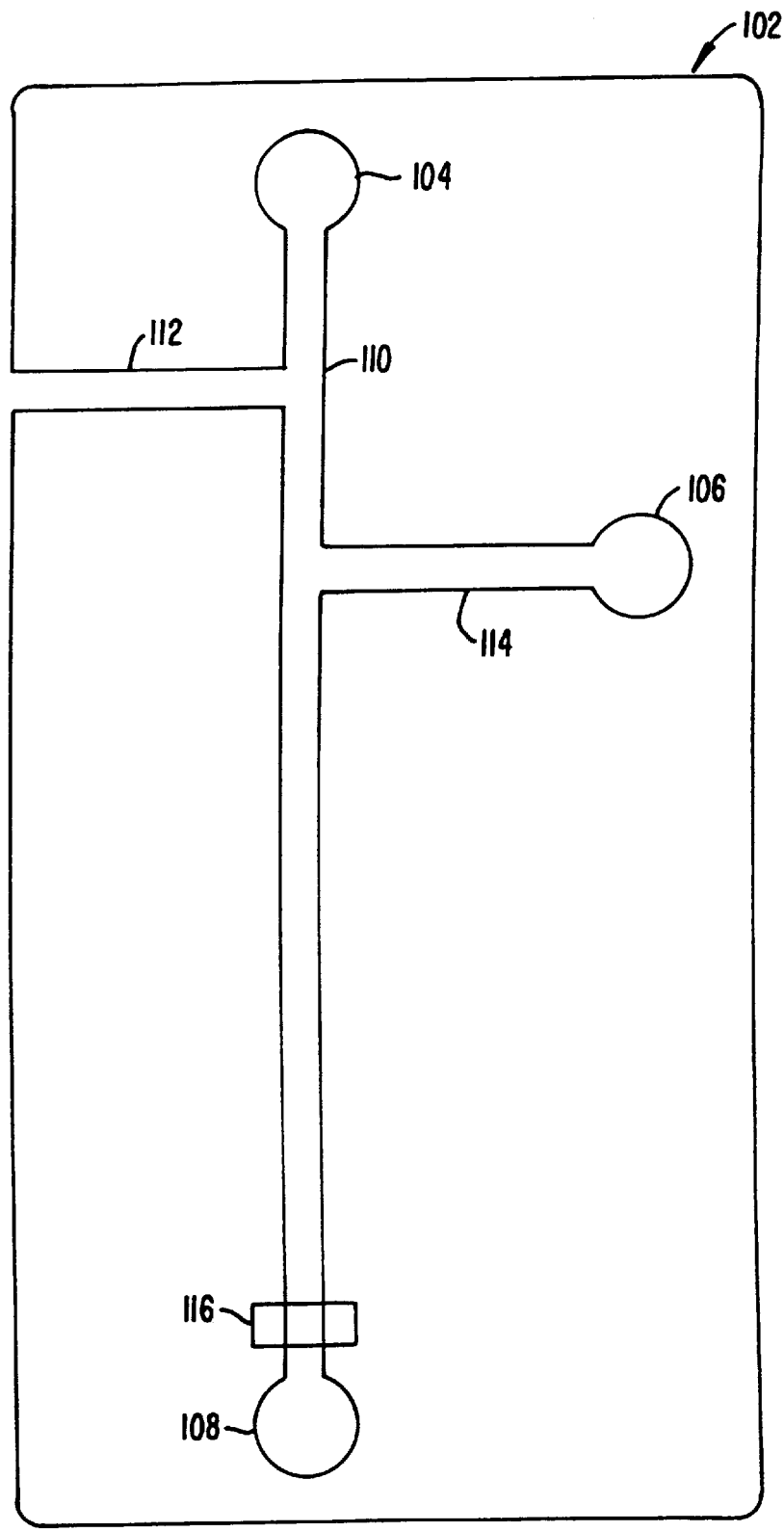
FIG. 1 is a schematic illustration of one embodiment of a microlaboratory screening assay system of the present invention which can be used in running a continuous flow assay system.

The present invention provides novel microlaboratory systems and methods that are useful for performing high-throughput screening assays. In particular, the present invention provides microfluidic devices and methods of using such devices in screening large numbers of different compounds for their effects on a variety of chemical, and preferably, biochemical systems.

As used herein, the phrase "biochemical system" generally refers to a chemical interaction that involves molecules of the type generally found within living organisms. Such interactions include the full range of catabolic and anabolic reactions which occur in living systems including enzymatic, binding, signalling and other reactions. Further, biochemical systems, as defined herein, also include model systems which are mimetic of a particular biochemical interaction. Examples of biochemical systems of particular interest in practicing the present invention include, e.g., receptor-ligand interactions, enzyme-substrate interactions, cellular signaling pathways, transport reactions involving model barrier systems (e.g., cells or membrane fractions) for bioavailability screening, and a variety of other general systems. Cellular or organismal viability or activity may also be screened using the methods and apparatuses of the present invention, e.g., in toxicology studies. Biological materials which are assayed include, but are not limited to, cells, cellular fractions (membranes, cytosol preparations, etc.), agonists and antagonists of cell membrane receptors (e.g., cell receptor-ligand interactions such as e.g., transferrin, c-kit, viral receptor ligands (e.g., CD4-HIV), cytokine receptors, chemokine receptors, interleukin receptors, immunoglobulin receptors and antibodies, the cadherein family, the integrin family, the selectin family, and the like; see, e.g., Pigott and Power (1993) *The Adhesion Molecule FactsBook* Academic Press New York and Hulme (ed) *Receptor Ligand Interactions A Practical Approach* Rickwood and Hames (series editors) IRL Press at Oxford Press NY), toxins and venoms, viral epitopes, hormones (e.g., opiates, steroids, etc.), intracellular receptors (e.g. which mediate the effects of various small ligands, including steroids, thyroid hormone, retinoids and vitamin D; for reviews see, e.g., Evans (1988) *Science*, 240:889–895; Ham and Parker (1989) *Curr. Opin. Cell Biol.*, 1:503–511; Burmstein et al. (1989), *Ann. Rev. Physiol.*, 51:683–699; Truss and Beato (1993) *Endocr. Rev.*, 14:459–479), peptides, retro-inverso peptides, polymers of $\alpha$-, $\beta$-, or $\omega$-amino acids (D- or L-), enzymes, enzyme substrates, cofactors, drugs, lectins, sugars, nucleic acids (both linear and cyclic polymer configurations), oligosaccharides, proteins, phospholipids and antibodies. Synthetic polymers such as heteropolymers in which a known drug is covalently bound to any of the above, such as polyurethanes, polyesters, polycarbonates, polyureas, polyamides, polyethyleneimines, polyarylene sulfides, polysiloxanes, polyimides, and polyacetates are also assayed. Other polymers are also assayed using the systems described herein, as would be apparent to one of skill upon review of this disclosure. One of skill will be generally familiar with the biological literature. For a general introduction to biological systems, see, Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, N.Y., (Sambrook); *Current Protocols in Molecular Biology*, F. M. Ausubel et al., eds., Current Protocols, a joint venture between Greene Publishing Associates, Inc. and John Wiley & Sons, Inc., (through 1997 Supplement) (Ausubel); Watson et al. (1987) *Molecular Biolojv of the Gene, Fourth Edition* The Benjamin/Cummings Publishing Co., Menlo Park, Calif.; Watson et al. (1992) Recombinant DNA Second Edition Scientific American Books, N.Y.; Alberts et al. (1989) *Molecular Biology of the Cell Second Edition* Garland Publishing, NY; Pattison (1994) *Principles and Practice of Clinical Virology;* Darnell et aL, (1990) *Molecular Cell Bioloy second edition,* Scientific American Books, W.H. Freeman and Company; Berkow (ed.) *The Merck Manual of Diagnosis and Therapy,* Merck & Co., Rahway, N.J.; *Harrison's Principles of Internal Medicine,* Thirteenth Edition, Isselbacher et al. (eds). (1994) Lewin *Genes,* 5th Ed., Oxford University Press (1994); The "Practical Approach" Series of Books (Rickwood and Hames (series eds.) by IRL Press at Oxford University Press, NY; The "FactsBook Series" of books from Academic Press, NY, ; Product information from manufacturers of biological reagents and experimental equipment also provide information useful in assaying biological systems. Such manufacturers include, e.g., the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

In order to provide methods and devices for screening compounds for effects on biochemical systems, the present invention generally incorporates model in vitro systems which mimic a given biochemical system in vivo for which effector compounds are desired. The range of systems against which compounds can be screened and for which effector compounds are desired, is extensive. For example, compounds are optionally screened for effects in blocking, slowing or otherwise inhibiting key events associated with biochemical systems whose effect is undesirable. For example, test compounds are optionally screened for their ability to block systems that are responsible, at least in part, for the onset of disease or for the occurrence of particular symptoms of diseases, including, e.g., hereditary diseases, cancer, bacterial or viral infections and the like. Compounds which show promising results in these screening assay methods can then be subjected to further testing to identify effective pharmacological agents for the treatment of disease or symptoms of a disease.

Alternatively, compounds can be screened for their ability to stimulate, enhance or otherwise induce biochemical systems whose function is believed to be desirable, e.g., to remedy existing deficiencies in a patient.

Once a model system is selected, batteries of test compounds can then be applied against these model systems. By identifying those test compounds that have an effect on the particular biochemical system, in vitro, one can identify potential effectors of that system, in vivo.

In their simplest forms, the biochemical system models employed in the methods and apparatuses of the present invention will screen for an effect of a test compound on an interaction between two components of a biochemical system, e.g., receptor-ligand interaction, enzyme-substrate interaction, and the like. In this form, the biochemical system model will typically include the two normally interacting components of the system for which an effector is sought, e.g., the receptor and its ligand or the enzyme and its substrate.

Determining whether a test compound has an effect on this interaction then involves contacting the system with the test compound and assaying for the functioning of the system, e.g., receptor-ligand binding or substrate turnover. The assayed function is then compared to a control, e.g., the same reaction in the absence of the test compound or in the presence of a known effector. Typically, such assays involve the measurement of a parameter of the biochemical system. By "parameter of the biochemical system" is meant some measurable evidence of the system's functioning, e.g., the presence or absence of a labeled group or a change in molecular weight (e.g., in binding reactions, transport screens), the presence or absence of a reaction product or substrate (in substrate turnover measurements), or an alteration in electrophoretic mobility (typically detected by a change in elution time of a labeled compound).

Although described in terms of two-component biochemical systems, the methods and apparatuses may also be used to screen for effectors of much more complex systems, where the result or end product of the system is known and assayable at some level, e.g., enzymatic pathways, cell signaling pathways and the like. Alternatively, the methods and apparatuses described herein are optionally used to screen for compounds that interact with a single component of a biochemical system, e.g., compounds that specifically bind to a particular biochemical compound, e.g., a receptor, ligand, enzyme, nucleic acid, structural macromolecule, etc.

Biochemical system models may also be embodied in whole cell systems. For example, where one is seeking to screen test compounds for an effect on a cellular response, whole cells are optionally utilized. Modified cell systems may also be employed in the screening systems encompassed herein. For example, chimeric reporter systems are optionally employed as indicators of an effect of a test compound on a particular biochemical system. Chimeric reporter systems typically incorporate a heterogenous reporter system integrated into a signaling pathway which signals the binding of a receptor to its ligand. For example, a receptor is fused to a heterologous protein, e.g., an enzyme whose activity is readily assayable. Activation of the receptor by ligand binding then activates the heterologous protein which then allows for detection. Thus, the surrogate reporter system produces an event or signal which is readily detectable, thereby providing an assay for receptor/ligand binding. Examples of such chimeric reporter systems have been previously described in the art.

Additionally, where one is screening for bioavailability, e.g., transport, biological barriers are optionally included. The term "biological barriers" generally refers to cellular or membranous layers within biological systems, or synthetic models thereof. Examples of such biological barriers include the epithelial and endothelial layers, e.g. vascular endothelia and the like.

Biological responses are often triggered and/or controlled by the binding of a receptor to its ligand. For example, interaction of growth factors, i.e., epidernal growth factor (EGF), fibroflost growth factor (FGF), platelet-dorwed growth factor (PDGF), etc., with their receptors stimulates a wide variety of biological responses including, e.g., cell proliferation and differentiation, activation of mediating enzymes, stimulation of messenger turnover, alterations in ion fluxes, activation of enzymes, changes in cell shape and the alteration in genetic expression levels. Accordingly, control of the interaction of the receptor and its ligand may offer control of the biological responses caused by that interaction.

Accordingly, in one aspect, the present invention will be useful in screening for compounds that affect an interaction between a receptor molecule and its ligands. As used herein, the term "receptor" generally refers to one member of a pair of compounds which specifically recognize and bind to each other. The other member of the pair is termed a "ligand." Thus, a receptor/ligand pair may include a typical protein receptor, usually membrane associated, and its natural ligand, e.g., another protein or small molecule. Receptor/ligand pairs may also include antibody/antigen binding pairs, complementary nucleic acids, nucleic acid associating proteins and their nucleic acid ligands. A large number of specifically associating biochemical compounds are well known in the art and can be utilized in practicing the present invention.

Traditionally, methods for screening for effectors of a receptor/ligand interaction have involved incubating a receptor/ligand binding pair in the presence of a test compound. The level of binding of the receptoriligand pair is then compared to negative and/or positive controls. Where a decrease in normal binding is seen, the test compound is determined to be an inhibitor of the receptor/ligand binding. Where an increase in that binding is seen, the test compound is determined to be an enhancer or inducer of the interaction.

In the interest of efficiency, screening assays have typically been set up in multiwell reaction plates, e.g., multiwell microplates, which allow for the simultaneous, parallel screening of large numbers of test compounds.

A similar, and perhaps overlapping, set of biochemical systems includes the interactions between enzymes and their substrates. The term "enzyme" as used herein, generally refers to a protein which acts as a catalyst to induce a chemical change in other compounds or "substrates."

Typically, effectors of an enzyme's activity toward its substrate are screened by contacting the enzyme with a substrate in the presence and absence of the compound to be screened and under conditions optimal for detecting changes in the enzyme's activity. After a set time for reaction, the mixture is assayed for the presence of reaction products or a decrease in the amount of substrate. The amount of substrate that has been catalyzed is them compared to a control, i.e. enzyme contacted with substrate in the absence of test compound or presence of a known effector. As above, a compound that reduces the enzymes activity toward its substrate is termed an "inhibitor," whereas a compound that accentuates that activity is termed an "inducer."

Generally, the various screening methods encompassed by the present invention involve the serial introduction of a plurality of test compounds into a microfluidic device. Once injected into the device, the test compound is screened for effect on a biological system using a continuous serial or parallel assay orientation.

As used herein, the term "test compound" refers to the collection of compounds that are to be screened for their ability to affect a particular biochemical system. Test compounds may include a wide variety of different compounds, including chemical compounds, mixtures of chemical compounds, e.g., polysaccharides, small organic or inorganic molecules, biological macromolecules, e.g., peptides, proteins, nucleic acids, or an extract made from biological materials such as bacteria, plants, fungi, or animal cells or tissues, naturally occurring or synthetic compositions. Depending upon the particular embodiment being practiced, the test compounds are provided, e.g., injected, free in solution, or are optionally attached to a carrier, or a solid support, e.g., beads. A number of suitable solid supports are employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, glass beads, polyaminemethylvinylether maleic acid copolymer, amino acid copolymer, ethylene-maleic acid copolymer, nylon, silk, etc. Additionally, for the methods and apparatuses described herein, test compounds are screened individually, or in groups. Group screening is particularly useful where hit rates for effective test compounds are expected to be low such that one would not expect more than one positive result for a given group. Alternatively, such group screening is used where the effects of different test compounds are differentially detected in a single system, e.g., through electrophoretic separation of the effects, or differential labelling which enables separate detection.

Test compounds are commercially available, or derived from any of a variety of biological sources apparent to one of skill and as described, supra. In one aspect, a tissue homogenate or blood sample from a patient is tested in the assay systems of the invention. For example, in one aspect, blood is tested for the presence or activity of a biologically relevant molecule. For example, the presence and activity level of an enzyme are detected by supplying and enzyme substrate to the biological sample and detecting the formation of a product using an assay systems of the invention. Similarly, the presence of infectious pathogens (viruses, bacteria, fungi, or the like) or cancerous tumors can be tested by monitoring binding of a labeled ligand to the pathogen or tumor cells, or a component of the pathogen or tumor such as a protein, cell membrane, cell extract or the like, or alternatively, by monitoring the presence of an antibody against the pathogen or tumor in the patient's blood. For example, the binding of an antibody from a patient's blood to a viral protein such as an HIV protein is a common test for monitoring patient exposure to the virus. Many assays for detecting pathogen infection are well known, and are adapted to the assay systems of the present invention.

Biological samples are derived from patients using well known techniques such as venipuncture or tissue biopsy. Where the biological material is derived from non-human animals, such as commercially relevant livestock, blood and tissue samples are conveniently obtained from livestock processing plants. Similarly, plant material used in the assays of the invention are conveniently derived from agricultural or horticultural sources. Alternatively, a biological sample can be from a cell or blood bank where tissue and/or blood are stored, or from an in vitro source such as a culture of cells. Techniques and methods for establishing a culture of cells for use as a source for biological materials are well known to those of skill in the art. Freshney *Culture of Animal Cells, a Manual of Basic Technique. Third Edition* Wiley-Liss, New York (1994) provides a general introduction to cell culture.

II. Assay Systems

As described above, the screening methods of the present invention are generally carried out in microfluidic devices or "microlaboratory systems," which allow for integration of the elements required for performing the assay, automation, and minimal environmental effects on the assay system, e.g., evaporation, contamination, human error, or the like. A number of devices for carrying out the assay methods of the invention are described in substantial detail below. However, it will be recognized that the specific configuration of these devices will generally vary depending upon the type of assay and/or assay orientation desired. For example, in some embodiments, the screening methods of the invention can be carried out using a microfluidic device having two intersecting channels. For more complex assays or assay orientations, multichannel/intersection devices are optionally employed. The small scale, integratability and self-contained nature of these devices allows for virtually any assay orientation to be realized within the context of the microlaboratory system.

A. Electrokinetic Material Transport

In preferred aspects, the devices, methods and systems described herein, employ electrokinetic material transport systems, and preferably, controlled electrokinetic material transport systems. As used herein, "electrokinetic material transport systems" include systems which transport and direct materials within an interconnected channel and/or chamber containing structure, through the application of electrical fields to the materials, thereby causing material movement through and among the channel and/or chambers, i.e., cations will move toward the negative electrode, while anions will move toward the positive electrode.

Such electrokinetic material transport and direction systems include those systems that rely upon the electrophoretic mobility of charged species within the electric field applied to the structure. Such systems are more particularly referred to as electrophoretic material transport systems. Other electrokinetic material direction and transport systems rely upon the electroosmotic flow of fluid and material within a channel or chamber structure which results from the application of an electric field across such structures. In brief, when a fluid is placed into a channel which has a surface bearing charged functional groups, e.g., hydroxyl groups in etched glass channels or glass microcapillaries, those groups can ionize. In the case of hydroxyl functional groups, this ionization, e.g., at neutral pH, results in the release of protons from the surface and into the fluid, creating a concentration of protons at near the fluid/surface interface, or a positively charged sheath surrounding the bulk fluid in the channel. Application of a voltage gradient across the length of the channel, will cause the proton sheath, as well as the fluid it surrounds, to move in the direction of the voltage drop, i.e., toward the negative electrode.

"Controlled electrokinetic material transport and direction," as used herein, refers to electrokinetic systems as described above, which employ active control of the voltages applied at multiple, i.e., more than two, electrodes. Rephrased, such controlled electrokinetic systems concomitantly regulate voltage gradients applied across at least two intersecting channels. Controlled electrokinetic material transport is described in Published PCT Application No. WO 96/04547, to Ramsey, which is incorporated herein by reference in its entirety for all purposes. In particular, the preferred microfluidic devices and systems described herein, include a body structure which includes at least two intersecting channels or fluid conduits, e.g., interconnected, enclosed chambers, which channels include at least three unintersected termini. The intersection of two channels refers to a point at which two or more channels are in fluid communication with each other, and encompasses "T" intersections, cross intersections, "wagon wheel" intersections of multiple channels, or any other channel geometry where two or more channels are in such fluid communication. An unintersected terminus of a channel is a point at which a channel terminates not as a result of that channel's intersection with another channel, e.g., a "T" intersection. In preferred aspects, the devices will include at least three intersecting channels having at least four unintersected termini. In a basic cross channel structure, where a single horizontal channel is intersected and crossed by a single vertical channel, controlled electrokinetic material transport operates to controllably direct material flow through the intersection, by providing constraining flows from the other channels at the intersection. For example, assuming one was desirous of transporting a first material through the horizontal channel, e.g., from left to right, across the intersection with the vertical channel. Simple electrokinetic material flow of this material across the intersection could be accomplished by applying a voltage gradient across the length of the horizontal channel, i.e., applying a first voltage to the left terminus of this channel, and a second, lower voltage to the right terminus of this channel, or by allowing the right terminus to float (applying no voltage). However, this type of material flow through the intersection would result in a substantial amount of diffusion at the intersection, resulting from both the natural diffusive properties of the material being transported in the medium used, as well as convective effects at the intersection.

In controlled electrokinetic material transport, the material being transported across the intersection is constrained by low level flow from the side channels, e.g., the top and bottom channels. This is accomplished by applying a slight voltage gradient along the path of material flow, e.g., from the top or bottom termini of the vertical channel, toward the right terminus. The result is a "pinching" of the material flow at the intersection, which prevents the diffusion of the material into the vertical channel. The pinched volume of material at the intersection may then be injected into the vertical channel by applying a voltage gradient across the length of the vertical channel, i.e., from the top terminus to the bottom terminus. In order to avoid any bleeding over of material from the horizontal channel during this injection, a low level of flow is directed back into the side channels, resulting in a "pull back" of the material from the intersection.

In addition to pinched injection schemes, controlled electrokinetic material transport is readily utilized to create virtual valves which include no mechanical or moving parts. Specifically, with reference to the cross intersection described above, flow of material from one channel segment to another, e.g., the left arm to the right arm of the horizontal channel, can be efficiently regulated, stopped and reinitiated, by a controlled flow from the vertical channel, e.g., from the bottom arm to the top arm of the vertical channel. Specifically, in the 'off' mode, the material is transported from the left arm, through the intersection and into the top arm by applying a voltage gradient across the left and top termini. A constraining flow is directed from the bottom arm to the top arm by applying a similar voltage gradient along this path (from the bottom terminus to the top terminus). Metered amounts of material are then dispensed from the left arm into the right arm of the horizontal channel by switching the applied voltage gradient from left to top, to left to right. The amount of time and the voltage gradient applied dictates the amount of material that will be dispensed in this manner. Although described for the purposes of illustration with respect to a four way, cross intersection, these controlled electrokinetic material transport systems can be readily adapted for more complex interconnected channel networks, e.g., arrays of interconnected parallel channels.

B. Continuous Flow Assay Systems

In one preferred aspect, the methods and apparatuses of the invention are used in screening test compounds using a continuous flow assay system. Generally, the continuous flow assay system can be readily used in screening for inhibitors or inducers of enzymatic activity, or for agonists or antagonists of receptor-ligand binding. In brief, the continuous flow assay system involves the continuous flow of the particular biochemical system along a microfabricated channel. As used herein, the term "continuous" generally refers to an unbroken or contiguous stream of the particular composition that is being continuously flowed. For example, a continuous flow may include a constant fluid flow having a set velocity, or alternatively, a fluid flow which includes pauses in the flow rate of the overall system, such that the pause does not otherwise interrupt the flow stream. The functioning of the system is indicated by the production of a detectable event or signal. In one preferred embodiment, such detectable signals include optically detectable chromophoric or fluorescent signals that are associated with the functioning of the particular model system used. For enzyme systems, such signals will generally be produced by products of the enzyme's catalytic action, e.g., on a chromogenic or fluorogenic substrate. For binding systems, e.g., receptor ligand interactions, signals will typically involve the association of a labeled ligand with the receptor, or vice versa.

A wide variety of other detectable signals and labels can also be used in the assays and apparatuses of the invention. In addition to the chromogenic and fluorogenic labels described above, radioactive decay, electron density, changes in pH, solvent viscosity, temperature and salt concentration are also conveniently measured.

More generally, labels are commonly detectable by spectroscopic, photochemical, biochemical, immunochemical, or chemical means. For example, useful nucleic acid labels include 32P, 35S, fluorescent dyes, electron-dense reagents, enzymes (e.g., as commonly used in an ELISA), biotin, dioxigenin, or haptens and proteins for which antisera or monoclonal antibodies are available. A wide variety of labels suitable for labeling biological components are known and are reported extensively in both the scientific and patent literature, and are generally applicable to the present invention for the labeling of biological components. Suitable labels include radionucleotides, enzymes, substrates, cofactors, inhibitors, fluorescent moieties, chemiluminescent moieties, magnetic particles, and the like. Labeling agents optionally include e.g., monoclonal antibodies, polyclonal antibodies, proteins, or other polymers such as affinity matrices, carbohydrates or lipids. Detection proceeds by any of a variety of known methods, including spectrophotometric or optical tracking of radioactive or fluorescent markers, or other methods which track a molecule based upon size, charge or affinity. A detectable moiety can be of any material having a detectable physical or chemical property. Such detectable labels have been well-developed in the field of gel electrophoresis, column chromatograpy, solid substrates, spectroscopic techniques, and the like, and in general, labels useful in such methods can be applied to the present invention. Thus, a label is any composition detectable by spectroscopic, photochemical, biochemical, immunochemical, electrical, optical thermal, or chemical means. Useful labels in the present invention include fluorescent dyes (e.g., fluorescein isothiocyanate, Texas red, rhodamine, and the like), radiolabels (e.g., 3H, 125I, 35S, 14C, 32P or 33P), enzymes (e.g., LacZ, chloramphenical acetyltronsferase CAT, horse radish peroxidase, alkaline phosphatase and others, commonly used as detectable enzymes, either as marker products or as in an ELISA), nucleic acid intercalators (e.g., ethidium bromide) and calorimetric labels such as colloidal gold or colored glass or plastic (e.g. polystyrene, polypropylene, latex, etc.) beads.

Fluorescent labels are particularly preferred labels. Preferred labels are typically characterized by one or more of the following: high sensitivity, high stability, low background, low environmental sensitivity and high specificity in labeling.

Fluorescent moieties, which are incorporated into the labels of the invention, are generally are known, including 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthen, 7-hydroxycoumarin, phenoxazine, calicylate, strophanthidin, porphyrins, triarylmethanes and flavin. Individual fluorescent compounds which have functionalities for linking to an element desirably detected in an apparatus or assay of the invention, or which can be modified to incorporate such functionalities include, e.g., dansyl chloride; fluoresceins such as 3,6-dihydroxy-9-phenylxanthhydrol; rhodamineisothiocyanate; N-phenyl 1-amino-8-sulfonatonaphthalene; N-phenyl 2-amino-6-sulfonatonaphthalene; 4-acetamido4-isothiocyanato-stilbene-2,2'-disulfonic acid; pyrene-3-sulfonic acid; 2-toluidinonaphthalene-6-sulfonate; N-phenyl-N-methyl-2-aminoaphthalene-6-sulfonate; ethidium bromide; stebrine; auromine-0,2-(9'-anthroyl)palmitate; dansyl phosphatidylethanolamine; N,N'-dioctadecyl oxacarbocyanine: N,N'-dihexyl oxacarbocyanine; merocyanine, 4-(3'pyrenyl) stearate; d-3-aminodesoxy-equilenin; 12-(9'-anthroyl) stearate; 2-methylanthracene; 9-vinylanthracene; 2,2' (vinylene-p-phenylene)bisbenzoxazole; p-bis(2-(4-methyl-5-phenyl-oxazolyl))benzene; 6-dimethylamino-1,2-benzophenazin; retinol; bis(3'-aminopyridinium) 1,10-decandiyl diiodide; sulfonaphthylhydrazone of hellibrienin; chlorotetracycline; N-($^7$-dimethylamino4-methyl-2-oxo-3-chromenyl)maleimide; N-(p-(2 -benzimidazolyl)-phenyl) maleimide; N-(4-fluoranthyl)maleimide; bis(homovanillic acid); resazarin; 4-chloro-7-nitro-2,1,3- benzooxadiazole; merocyanine 540; resorufin; rose bengal; and 2,4-diphenyl-3(2H)-furanone. Many fluorescent tags are commercially available from SIGMA chemical company (Saint Louis, Mo.), Molecular Probes, R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), and Applied Biosystems (Foster City, Calif.) as well as other commercial sources known to one of skill.

Desirably, fluorescent labels absorb light above about 300 nm, preferably about 350 nm, and more preferably above about 400 nm, usually emitting at wavelengths greater than about 10 nm higher than the wavelength of the light absorbed. It should be noted that the absorption and emission characteristics of the bound label may differ from the unbound label. Therefore, when referring to the various wavelength ranges and characteristics of the labels, it is intended to indicate the labels as employed and not the label which is unconjugated and characterized in an arbitrary solvent.

Fluorescent labels are one preferred class of detectable labels, in part because by irradiating a fluorescent label with light, one can obtain a plurality of emissions. Thus, a single label can provide for a plurality of measurable events. Detectable signal may also be provided by chemiluminescent and bioluminescent sources. Chemiluminescent sources include a compound which becomes electronically excited by a chemical reaction and may then emit light which serves as the detectible signal or donates energy to a fluorescent acceptor. A diverse number of families of compounds have been found to provide chemiluminescence under a variety or conditions. One family of compounds is 2,3-dihydro-1,4-phlthlazinedione. The most popular compound is luminol, which is a 5-amino compound. Other members of the family include the 5-amino-6,7,8-trimethoxy- and the dimethylamino [ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents, Chemiluminescence may also be obtained with oxalates, usually oxalyl active esters, e.g., p-nitrophenyl and a peroxide, e.g., hydrogen peroxide, under basic conditions. Other useful chemiluminescent compounds are also known and available, including -N-alkyl acridinum esters (basic $H_2O_2$) and dioxetanes. Alternatively, luciferins may be used in conjunction with luciferase or lucigenins to provide bioluminescence.

The label is coupled directly or indirectly to a molecule to be detected (a product, substrate, enzyme, or the like) according to methods well known in the art. As indicated above, a wide variety of labels are used, with the choice of label depending on the sensitivity required, ease of conjugation of the compound, stability requirements, available instrumentation, and disposal provisions. Non radioactive labels are often attached by indirect means. Generally, a ligand molecule (e.g., biotin) is covalently bound to a polymer. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with labeled, anti-ligands. Alternatively, any haptenic or antigenic compound can be used in combination with an antibody. Labels can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as digital cameras, charge coupled devices (CCDs) or photomultipliers and phototubes, and the like. Fluorescent labels and detection techniques, particularly microscopy and spectroscopy are preferred. Similarly, enzymatic labels are detected by providing appropriate substrates for the enzyme and detecting the resulting reaction product. Finally, simple colorimetric labels are often detected simply by observing the color associated with the label. For example, conjugated gold often appears pink, while various conjugated beads appear the color of the bead.

In preferred aspects, the continuous system generates a constant signal which varies only when a test compound is introduced that affects the system. Specifically, as the system components flow along the channel, they will produce a relatively constant signal level at a detection zone or window of the channel. Test compounds are periodically introduced into the channel and mixed with the system components. Where those test compounds have an effect on the system, it will cause a deviation from the constant signal level at the detection window. This deviation may then be correlated to the particular test compound screened.

One embodiment of a device for use in a serial or continuous assay geometry is shown in FIG. 1. As shown, the overall device 100 is fabricated in a planar substrate 102. Suitable substrate materials are generally selected based upon their compatibility with the conditions present in the particular operation to be performed by the device. Such conditions can include extremes of pH, temperature, salt concentration, and application of electrical fields. Additionally, substrate materials are also selected for their inertness to critical components of an analysis or synthesis to be carried out by the device.

Examples of useful substrate materials include, e.g., glass, quartz and silicon as well as polymeric substrates, e.g. plastics. In the case of conductive or semi-conductive substrates, it will generally be desirable to include an insulating layer on the substrate. This is particularly important where the device incorporates electrical elements, e.g., electrical material and fluid direction systems, sensors and the like. In the case of polymeric substrates, the substrate materials are optionally rigid, semi-rigid, or non-rigid, opaque, semi-opaque or transparent, depending upon the use for which they are intended. For example, devices which include an optical or visual detection element, will generally be fabricated, at least in part, from transparent materials to allow, or at least, facilitate that detection. Alternatively, transparent windows of, e.g., glass or quartz, are optionally incorporated into the device for these types detection elements. Additionally, the polymeric materials may have linear or branched backbones, and are optionally crosslinked or non-crosslinked. Examples of particularly preferred polymeric materials include, e.g., polydimethylsiloxanes (PDMS), polyurethane, polyvinylchloride (PVC) polystyrene, polysulfone, polycarbonate and the like.

The device shown in FIG. 1 includes a series of channels 110, 112, and optional reagent channel 114, fabricated into the surface of the substrate. At least one of these channels will typically have very small cross sectional dimensions, e.g., in the range of from about 0.1 $\mu$m to about 500 $\mu$m. Preferably the cross-sectional dimensions of the channels will be in the range of from about 0.1 to about 200 $\mu$m and more preferably in the range of from about 0.1 to about 100 $\mu$m. In particularly preferred aspects, each of the channels will have at least one cross-sectional dimension in the range of from about 0.1 $\mu$m to about 100 $\mu$m. Although generally shown as straight channels, it will be appreciated that in order to maximize the use of space on a substrate, serpentine, saw tooth or other channel geometries, to incorporate effectively longer channels in shorter distances.

Manufacturing of these microscale elements into the surface of the substrates may generally be carried out by any number of microfabrication techniques that are well known in the art. For example, lithographic techniques are optionally employed in fabricating, e.g., glass, quartz or silicon substrates, using methods well known in the semiconductor manufacturing industries such as photolithographic etching, plasma etching or wet chemical etching. Alternatively, micromachining methods such as laser drilling, micromilling and the like are optionally employed. Similarly, for polymeric substrates, well known manufacturing techniques may also be used. These techniques include injection molding or stamp molding methods where large numbers of substrates are optionally produced using, e.g., rolling stamps to produce large sheets of microscale substrates or polymer microcasting techniques where the substrate is polymerized within a micromachined mold.

The devices will typically include an additional planar element which overlays the channeled substrate enclosing and fluidly sealing the various channels to form conduits. Attaching the planar cover element is achieved by a variety of means, including, e.g., thermal bonding, adhesives or, in the case of certain substrates, e.g., glass, or semi-rigid and non-rigid polymeric substrates, a natural adhesion between the two components. The planar cover element may additionally be provided with access ports and/or reservoirs for introducing the various fluid elements needed for a particular screen.

The device shown in FIG. 1 also includes reservoirs 104, 106 and 108, disposed and fluidly connected at the ends of the channels 110 and 114. As shown, sample channel 112, is used to introduce the plurality of different test compounds into the device. As such, this channel will generally be fluidly connected to a source of large numbers of separate test compounds that will be individually introduced into the sample channel 112 and subsequently into channel 110.

The introduction of large numbers of individual, discrete volumes of test compounds into the sample is carried out by a number of methods. For example, micropipettors are optionally used to introduce the test compounds into the device. In preferred aspects, an electropipettor is used which is fluidly connected to sample channel 112. An example of such an electropipettor is described in, e.g., U.S. Pat. No. 5,779,868 the disclosure of which is hereby incorporated herein by reference in its entirety for all purposes. Generally, this electropipettor utilizes electroosmotic fluid direction as described herein, to alternately sample a number of test compounds, or "subject materials," and spacer compounds. The pipettor then delivers individual, physically isolated sample or test compound volumes in subject material regions, in series, into the sample channel for subsequent manipulation within the device. Individual samples are typically separated by a spacer region of low ionic strength spacer fluid. These low ionic strength spacer regions have higher voltage drop over their length than do the higher ionic strength subject material or test compound regions, thereby driving the electrokinetic pumping. On either side of the test compound or subject material region, which is typically in higher ionic strength solution, are fluid regions referred to as first spacer regions (also referred to as "guard bands"), that contact the interface of the subject material regions. These first spacer regions typically comprise a high ionic strength solution to prevent migration of the sample elements into the lower ionic strength fluid regions, or second spacer region, which would result in electrophoretic bias. The use of such first and second spacer regions is described in greater detail in U.S. Pat. No. 5,779,868 which is incorporated herein by reference.

Alternatively, the sample channel 112 is optionally individually fluidly connected to a plurality of separate reservoirs via separate channels. The separate reservoirs each contain a separate test compound with additional reservoirs being provided for appropriate spacer compounds. The test compounds and/or spacer compounds are then transported from the various reservoirs into the sample channels using appropriate material direction schemes. In either case, it generally is desirable to separate the discrete sample volumes, or test compounds, with appropriate spacer regions.

As shown, the device also includes a detection window or zone 116 at which a signal from the biochemical system is optionally monitored. This detection window typically will include a transparent cover allowing visual or optical observation and detection of the assay results, e.g., observation of a colorometric or fluorometric response.

In particularly preferred aspects, monitoring of the signals at the detection window is achieved using an optical detection system. For example, fluorescence based signals are typically monitored using, e.g., laser activated fluorescence detection systems which employ a laser light source at an appropriate wavelength for activating the fluorescent indicator within the system. Fluorescence is then detected using an appropriate detector element, e.g., a photomultiplier tube (PMT). Similarly, for screens employing colorometric signals, spectrophotometric detection systems which direct a light source at the sample are optionally used, providing a measurement of absorbance or transmissivity of the sample.

In alternative aspects, the detection system may comprise non-optical detectors or sensors for detecting a particular characteristic of the system disposed within detection window 116. Such sensors may include temperature, conductivity, potentiometric (pH, ions), amperometric (for compounds that are oxidized or reduced, e.g., $O_2$, $H_2O_2$, $I_2$, oxidizable/reducible organic compounds, and the like).

In operation, a flowable first component of a biological system, e.g., a fluid comprising a receptor or enzyme, is placed in reservoir 104. This first component is flowed through main channel 110, past the detection window, 116, and toward waste reservoir 108. A second component of the biochemical system, e.g., a ligand or substrate, is concurrently flowed into the main channel 110 from the side channel 114, whereupon the first and second components mix and are able to interact. Deposition of these elements within the device is carried out in a number of ways. For example, the enzyme and substrate, or receptor and ligand solutions can be introduced into the device through open or sealable access ports in the planar cover. Alternatively, these components are optionally added to their respective reservoirs during manufacture of the device. In the case of such pre-added components, it is desirable to provide these components in a stabilized form to allow for prolonged shelf-life of the device. For example, the enzyme/substrate or receptor/ligand components are optionally provided within the device in lyophilized form. Prior to use, these components are easily reconstituted by introducing a buffer solution into the reservoirs. Alternatively, the components are lyophilized with appropriate buffering salts, whereby simple water addition is all that is required for reconstitution.

As noted above, the interaction of the first and second components is typically accompanied by a detectable signal. For example, in those embodiments where the first component is an enzyme and the second a substrate, the substrate is a chromogenic or fluorogenic substrate which produces an optically detectable signal when the enzyme acts upon the substrate. In the case where the first component is a receptor and the second is a ligand, either the ligand or the receptor optionally includes a detectable signal. In either event, the mixture and flow rate of compounds will typically remain constant such that the flow of the mixture of the first and second components past the detection window 116 will produce a steady-state signal. By "steady state signal" is generally meant a signal that has a regular, predictable signal intensity profile. As such, the steady-state signal may include signals having a constant signal intensity, or alternatively, a signal with a regular periodic intensity, against which variations in the normal signal profile is measured. This latter signal is generated in cases where fluid flow is periodically interrupted for, e.g., loading additional test compounds, as described in the description of the continuous flow systems. Although the signal produced in the above-described enzymatic system will vary along the length of the channel, i.e., increasing with time of exposure as the enzyme converts the fluorogenic substrate to the fluorescent product, the signal at any specific point along the channel will remain constant, given a constant flow rate.

From sample channel 112, test compounds is periodically or serially introduced into the main channel 110 and into the stream of first and second components as fluid regions containing the test compound, also referred to as the "subject material regions." Where these test compounds have an effect on the interaction of the first and second elements, it will produce a deviation in the signal detected at the detection window corresponding to the subject material region. As noted above, typically, the various different test compounds to be injected through channel 112 will be separated by a first and even second spacer fluid regions to allow differentiation of the effects, or lack of effects, from one test compound to another. In those embodiments where electroosmotic fluid direction systems are employed, the spacer fluid regions may also function to reduce any electrophoretic bias that can occur within the test sample. The use of these spacer regions to drive the electroosmotic flow of fluids, as well as in the general elimination of electrophoretic bias within the sample or test compound or subject material regions is substantially described in U.S. Pat. No. 5,779,868, previously incorporated herein by reference.

By way of example, a steady, continuous flow of enzyme and fluorogenic substrate through main channel 110 will produce a constant fluorescent signal at the detection window 116. Where a test compound inhibits the enzyme, introduction of a test compound, i.e., in a subject material region, will produce a momentary but detectable drop in the level of signal at the detection window corresponding with that subject material region. The timing of the drop in signal can then be correlated with a particular test compound based upon a known injection to detection time-frame. Specifically, the time required for an injected compound to produce an observed effect can be readily determined using positive controls.

For receptor/ligand systems, a similar variation in the steady state signal may also be observed. Specifically, the receptor and its fluorescent ligand can be made to have different flow rates along the channel. This can be accomplished by incorporating size exclusion matrices within the channel, or, in the case of electroosmotic methods, altering the relative electrophoretic mobility of the two compounds so that the receptor flows more rapidly down the channel. Again, this is accomplished through the use of size exclusion matrices, or through the use of different surface charges in the channel which will result in differential flow rates of charge-varied compounds. Where a test compound binds to the receptor, it will result in a dark pulse in the fluorescent signal followed by a brighter pulse. Without being bound to a particular theory of operation, it is believed that the steady state signal is a result of both free fluorescent ligand, and fluorescent ligand bound to the receptor. The bound ligand is traveling at the same flow rate as the receptor while the unbound ligand is traveling more slowly. Where the test compound inhibits the receptor-ligand interaction, the receptor will not 'bring along' the fluorescent ligand, thereby diluting the fluorescent ligand in the direction of flow, and leaving an excess of free fluorescent ligand behind. This results in a temporary reduction in the steady-state signal, followed by a temporary increase in fluorescence. Alternatively, schemes similar to those employed for the enzymatic system is employed, where there is a signal that reflects the interaction of the receptor with its ligand. For example, pH indicators which indicate pH effects of receptor-ligand binding is incorporated into the device along with the biochemical system, i.e., in the form of encapsulated cells, whereby slight pH changes resulting from binding can be detected. See Weaver, et al., *Bio/Technology* (1988) 6:1084–1089. Additionally, one can monitor activation of enzymes resulting from receptor ligand binding, e.g., activation of kinases, or detect conformational changes in such enzymes upon activation, e.g., through incorporation of a fluorophore which is activated or quenched by the conformational change to the enzyme upon activation.

Flowing and direction of fluids within the microscale fluidic devices is carried out by a variety of methods. For example, the devices may include integrated microfluidic structures, such as micropumps and microvalves, or external elements, e.g., pumps and switching valves, for the pumping and direction of the various fluids through the device. Examples of microfluidic structures are described in, e.g., U.S. Pat. Nos. 5,271,724, 5,277,556, 5,171,132, and 5,375, 979. See also, Published U.K. Patent Application No. 2 248 891 and Published European Patent Application No. 568 902.

Although microfabricated fluid pumping and valving systems are readily employed in the devices of the invention, the cost and complexity associated with their manufacture and operation can generally prohibit their use in mass-produced disposable devices as are envisioned by the present invention. For that reason, in particularly preferred aspects, the devices of the invention will typically include an electroosmotic fluid direction system. Such fluid direction systems combine the elegance of a fluid direction system devoid of moving parts, with an ease of manufacturing, fluid control and disposability. Examples of particularly preferred electroosmotic fluid direction systems include, e.g., those described in International Patent Application No. WO 96/04547 to Ramsey et al., which is incorporated herein by reference in its entirety for all purposes.

In brief, these fluidic control systems typically include electrodes disposed within the reservoirs that are placed in fluid connection with the plurality of intersecting channels fabricated into the surface of the substrate. The materials stored in the reservoirs are transported through the channel system delivering appropriate volumes of the various materials to one or more regions on the substrate in order to carry out a desired screening assay.

Fluid and materials transport and direction is accomplished through electroosmosis or electrokinesis. In brief, when an appropriate material, typically comprising a fluid, is placed in a channel or other fluid conduit having functional groups present at the surface, those groups can ionize. For example, where the surface of the channel includes hydroxyl functional groups at the surface, protons can leave the surface of the channel and enter the fluid. Under such conditions, the surface will possess a net negative charge, whereas the fluid will possess an excess of protons or positive charge, particularly localized near the interface between the channel surface and the fluid. By applying an electric field along the length of the channel, cations will flow toward the negative electrode. Movement of the positively charged species in the fluid pulls the solvent with them. The steady state velocity of this fluid movement is generally given by the equation:

$$v = \frac{\epsilon \xi E}{4\pi \eta}$$

where v is the solvent velocity, $\epsilon$ is the dielectric constant of the fluid, $\xi$ is the zeta potential of the surface, E is the electric field strength, and $\eta$ is the solvent viscosity. Thus, as can be easily seen from this equation, the solvent velocity is directly proportional to the surface potential.

To provide appropriate electric fields, the system generally includes a voltage controller that is capable of applying selectable voltage levels, simultaneously, to each of the reservoirs, including ground. Such a voltage controller can be implemented using multiple voltage dividers and multiple relays to obtain the selectable voltage levels. Alternatively, multiple, independent voltage sources are optionally used. The voltage controller is electrically connected to each of the reservoirs via an electrode positioned or fabricated within each of the plurality of reservoirs.

Incorporating this electroosmotic fluid direction system into the device shown in FIG. 1 involves incorporation of an electrode within each of the reservoirs 104, 106 and 108, and at the terminus of sample channel 112 or at the terminus of any fluid channels connected thereto, whereby the electrode is in electrical contact with the fluid disposed in the respective reservoir or channel. Substrate materials are also selected to produce channels having a desired surface charge. In the case of glass substrates, the etched channels will possess a net negative charge resulting from the ionized hydroxyls naturally present at the surface. Alternatively, surface modifications are optionally employed to provide an appropriate surface charge, e.g., coatings, derivatization, e.g., silanation, or impregnation of the surface to provide appropriately charged groups on the surface. Examples of such treatments are described in, e.g., Provisional Patent Application Ser. No. 60/015,498, filed Apr. 16, 1996 (abandoned') which is hereby incorporated herein by reference in its entirety for all purposes.

In brief, suitable substrate materials are generally selected based upon their compatibility with the conditions present in the particular operation to be performed by the device. Such conditions can include extremes of pH, temperature and salt concentration. Additionally, substrate materials are also selected for their inertness to critical components of an analysis or synthesis to be carried out by the device. Polymeric substrate materials may be rigid, semi-rigid, or non-rigid, opaque, semi-opaque or. transparent, depending upon the use for which they are intended. For example, devices which include an optical or visual detection element, will generally be fabricated, at least in part, from a transparent polymeric material to facilitate that detection. Alternatively, transparent windows of , e.g. glass or quartz, may be incorporated into the device for these detection elements. Additionally, the polymeric materials may have linear or branched backbones, and may be crosslinked or non-crosslinked. Examples of polymeric materials include, e.g., Acrylics, especially PMMAs (polymethylmethacrylates); exemplar acrylics include e.g., Acrylite M-30 or Acrylite L40 available from CYRO Industries, Rockaway, N.J., or PLEXIGLAS VS UVT available from Autohaas North America; polycarbonates (e.g., Makrolon CD-2005 available from The Plastics and Rubber division of Mobay Corporation (Pittsburg, Pa.) or Bayer Corporation, or LEXAN OQ 1020L or LEXAN OQ 1020, both available from GE Plastics) polydimethylsiloxanes (PDMS), polyurethane, polyvinyichioride (PVC) polystyrene, polysulfone, polycarbonate and the like. Optical, mechanical, thermal, electrical, and chemical resistance properties for many plastics are well known (and are generally available from the manufacturer), or can easily be determined by standard assays.

As described herein, the electrokinetic fluid control systems employed in the devices of the present invention generally utilize a substrate having charged functional groups at its surface, such as the hydroxyl groups present on glass surfaces. As described, devices of the present invention can also employ plastic or other polymeric substrates. In general, these substrate materials have hydrophobic surfaces. As a result, use of electrokinetic fluid control systems in devices utilizing polymeric substrates used in the present invention typically employs modification of the surfaces of the substrate that are in contact with fluids.

Surface modification of polymeric substrates may take on a variety of different forms. For example, surfaces may be coated with an appropriately charged material. For example, surfactants with charged groups and hydrophobic tails are desirable coating materials. In short, the hydrophobic tails will localize to the hydrophobic surface of the substrate, thereby presenting the charged head group at the fluid layer.

In one embodiment, preparation of a charged surface on the substrate involves the exposure of the surface to be modified, e.g., the channels and/or reaction chambers, to an appropriate solvent which partially dissolves or softens the surface of the polymeric substrate. A detergent is then contacted with the partially dissolved surface. The hydrophobic portion of the detergent molecules will associate with the partially dissolve polymer. The solvent is then washed from the surface, e.g., using water, whereupon the polymer surface hardens with the detergent embedded into the surface, presenting the charged head group to the fluid interface.

In alternative aspects, polymeric materials, such as polydimethylsiloxane, may be modified by plasma irradiation. In particular, plasma irradiation of PDMS oxidizes the methyl groups, liberating the carbons and leaving hydroxyl groups in their place, effectively creating a glass-like surface on the polymeric material, with its associated hydroxyl functional groups.

The polymeric substrate may be rigid, semi-rigid, non-rigid or a combination of rigid and nonrigid elements, depending upon the particular application for which the device is to be used. In one embodiment, a substrate is made up of at least one softer, flexible substrate element and at least one harder, more rigid substrate element, one of which includes the channels and chambers manufactured into its surface. Upon mating the two substrates, the inclusion of the soft element allows formation of an effective fluid seal for the channels and chambers, obviating the need and problems associated with gluing or melting more rigid plastic components together.

A number of additional elements are added to the polymeric substrate to provide for the electrokinetic fluid control systems. These elements may be added either during the substrate formation process, i.e., during the molding or stamping steps, or they may be added during a separate, subsequent step. These elements typically include electrodes for the application of voltages to the various fluid reservoirs, and in some embodiments, voltage sensors at the various channel intersections to monitor the voltage applied.

Electrodes may be incorporated as a portion of the molding process. In particular, the electrodes may be patterned within the mold so that upon introduction of the polymeric material into the mold, the electrodes will be appropriately placed. Alternatively, the electrodes and other elements may be added after the substrate is formed, using well known microfabrication methods, e.g., sputtering or controlled vapor deposition methods followed by chemical etching.

Whether polymeric or other substrates are used, modulating voltages are concomitantly applied to the various reservoirs to affect a desired fluid flow characteristic, e.g., continuous flow of receptor/enzyme, ligand/substrate toward the waste reservoir with the periodic introduction of test compounds. Particularly, modulation of the voltages applied at the various reservoirs can move and direct fluid flow through the interconnected channel structure of the device in a controlled manner to effect the fluid flow for the desired screening assay and apparatus.

Figure 2A:
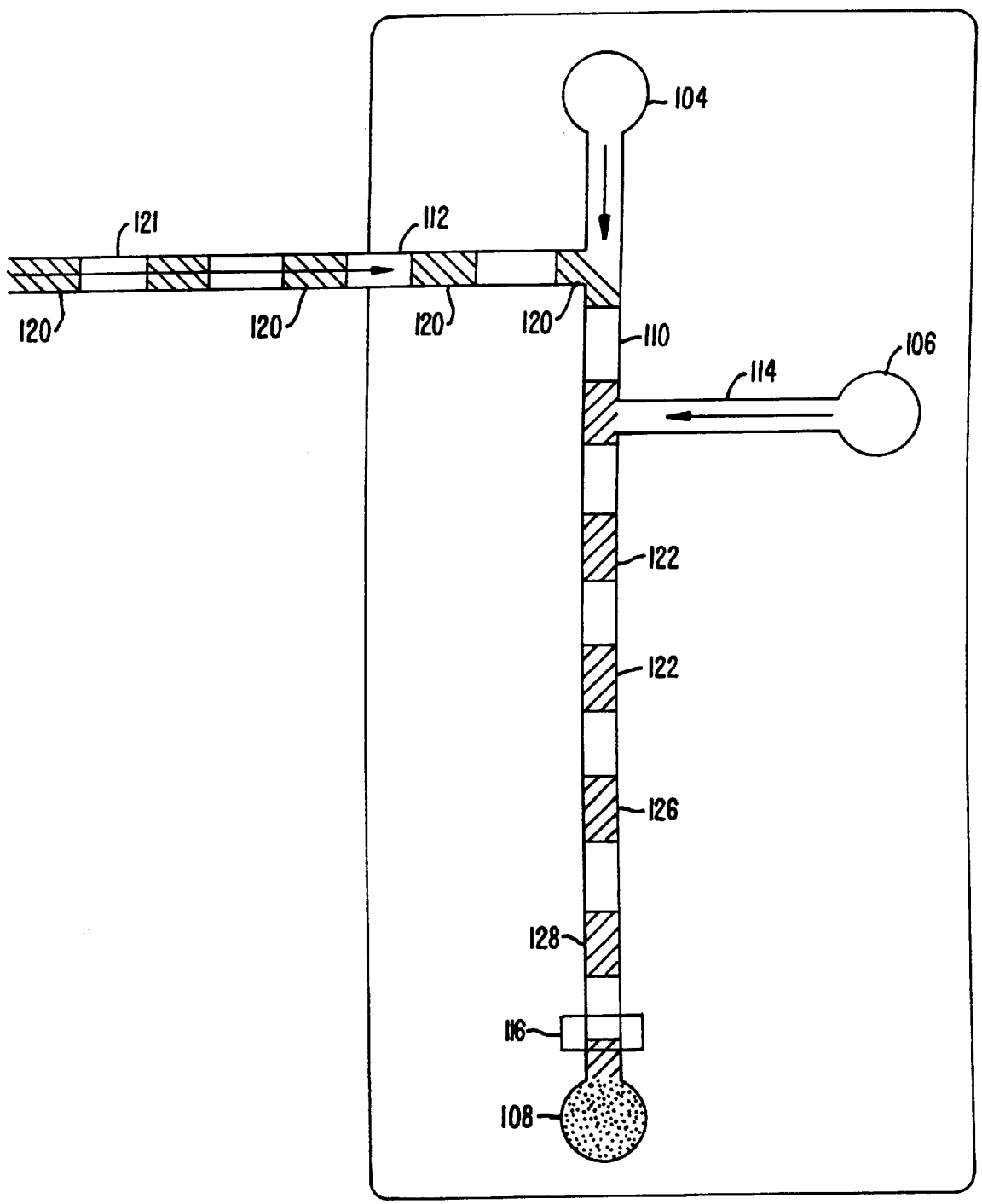
FIGS. 2A and 2B show a schematic illustration of the apparatus shown in FIG. 1, operating in alternate assay systems.

FIG. 2A shows a schematic illustration of fluid direction during a typical assay screen. Specifically, shown is the injection of a test compound (in a subject material region) into a continuous stream of an enzyme-fluorogenic substrate mixture. As shown in FIG. 2A, and with reference to FIG. 1, a continuous stream of enzyme is flowed from reservoir 104, along main channel 110. Test compounds 120, separated by appropriate spacer regions 121, e.g., low ionic strength spacer regions, are introduced from sample channel 112 into main channel 110. Once introduced into the main channel, the test compounds will interact with the flowing enzyme stream. The mixed enzyme/test compound regions are then flowed along main channel 110 past the intersection with channel 114. A continuous stream of fluorogenic or chromogenic substrate which is contained in reservoir 106, is introduced into sample channel 110, whereupon it contacts and mixes with the continuous stream of enzyme, including the subject material regions which include the test compounds 122. Action of the enzyme upon the substrate will produce an increasing level of the fluorescent or chromatic signal. This increasing signal is indicated by the increasing shading within the main channel as it approaches the detection window. This signal trend will also occur within those test compound or subject material regions which have no effect on the enzyme/substrate interaction, e.g., test compound 126. Where a test compound does have an effect on the interaction of the enzyme and the substrate, a variation will appear in the signal produced. For example, assuming a fluorogenic substrate, a test compound which inhibits the interaction of the enzyme with its substrate will result in less fluorescent product being produced within that subject material region. This will result in a non-fluorescent, or detectably less fluorescent region within the flowing stream as it passes detection window 116, which corresponds to the subject material region. For example, as shown, a subject material region including a test compound 128, which is a putative inhibitor of the enzyme-substrate interaction, shows detectably lower fluorescence than the surrounding stream. This is indicated by a lack of shading of subject material region 128.

A detector adjacent to the detection window monitors the level of fluorescent signal being produced by the enzyme's activity on the fluorogenic or chromogenic substrate. This signal remains at a relatively constant level for those test compounds which have no effect on the enzyme-substrate interaction. When an inhibitory compound is screened, however, it will produce a momentary drop in the fluorescent signal representing the reduced or inhibited enzyme activity toward the substrate. Conversely, inducer compounds, upon screening, produce a momentary increase in the fluorescent signal, corresponding to the increased enzyme activity toward the substrate.

Figure 2B:
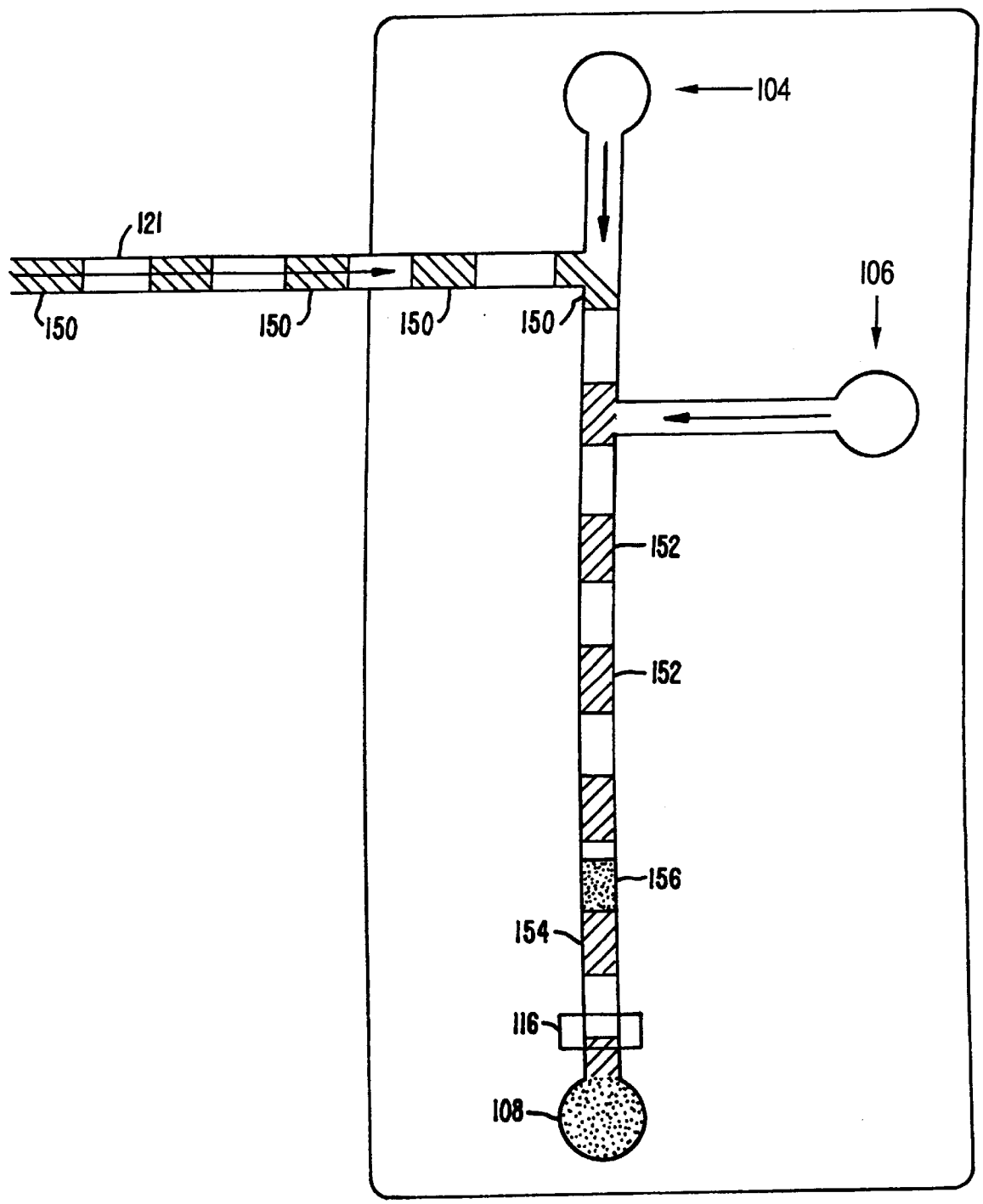

FIG. 2B provides a similar schematic illustration of a screen for effectors of a receptor-ligand interaction. As in FIG. 2A, a continuous stream of receptor is flowed from reservoir 104 through main channel 110. Test compounds or subject material regions 150 separated by appropriate spacer fluid regions 121 are introduced into the main channel 110 from sample channel 112, and a continuous stream of fluorescent ligand from reservoir 106 is introduced from side channel 114. Fluorescence is indicated by shading within the channel. As in FIG. 2A, the continuous stream of fluorescent ligand and receptor past the detection window 116 will provide a constant signal intensity. The subject material regions in the stream, containing the test compounds which have no effect on the receptor-ligand interaction, will provide the same or similar level of fluorescence as the rest of the surrounding stream, e.g., test compound or subject material region 152. However, the presence of test compounds which possess antagonistic or inhibitory activity toward the receptor-ligand interaction will result in lower levels of that interaction in those portions of the stream where those compounds are located, e.g., test compound or subject material region 154. Further, differential flow rates for the receptor bound fluorescent ligand and free fluorescent ligand will result in a detectable drop in the level of fluorescence which corresponds to the dilution of the fluorescence resulting from unbound, faster moving receptor. The drop in fluorescence is then followed by an increase in fluorescence 156 which corresponds to an accumulation of the slower moving, unbound fluorescent ligand.

In some embodiments, it is desirable to provide an additional channel for shunting off or extracting the subject material region reaction mixture from the running buffer and/or spacer regions. This may be the case where one wishes to keep the reaction elements contained within the a discrete fluid region during the reaction, while allowing these elements to be separated during a data acquisition stage. As described previously, one can keep the various elements of the reaction together in the subject material region that is moving through the reaction channel by incorporating appropriate spacer fluid regions between samples. Such spacer fluid regions are generally selected to retain the samples within their original subject material regions, i.e., not allowing smearing of the sample into the spacer regions, even during prolonged reaction periods. However, this goal can be at odds with those assays which are based upon the separation of elements of the assay, e.g., ligand-receptor assays described above, or where a reaction product must be separated in a capillary. Thus, it may be desirable to remove those elements which prevented such separation during the initial portions of the fluid direction.

Figure 5:
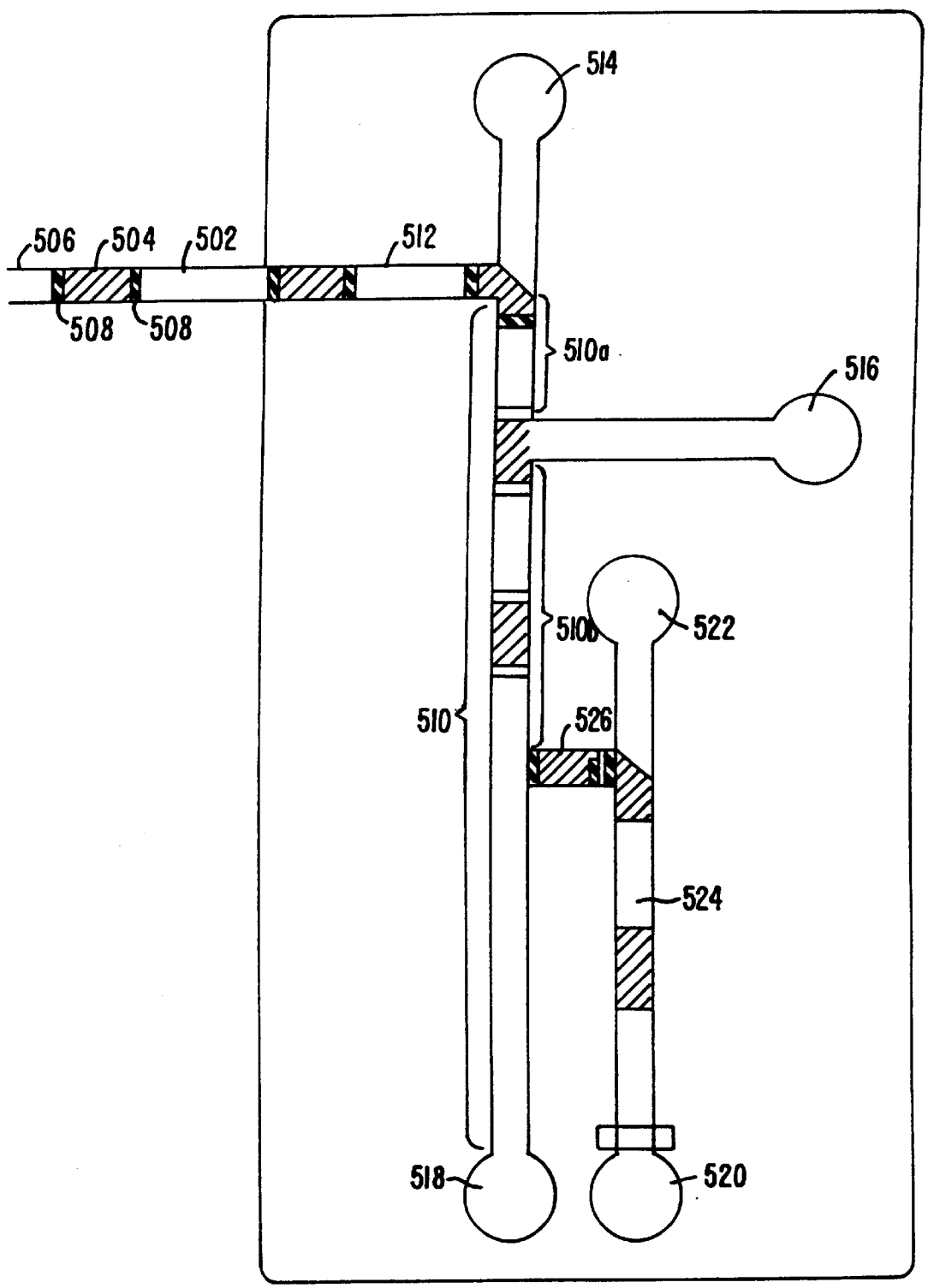
FIG. 5 shows a schematic illustration of a continuous flow assay device incorporating a sample shunt for performing prolonged incubation followed by a separation step.

A schematic illustration of one embodiment of a device 500 for performing this sample or subject material shunting or extraction is shown in FIG. 5. As shown, the subject materials or test compounds 504 are introduced to the device or chip via the sample channel 512. Again, these are typically introduced via an appropriate injection device 506, e.g., a capillary pipettor. The ionic strength and lengths of the first spacer regions 508 and second spacer regions 502 are selected such that those samples with the highest electrophoretic mobility will not migrate through the first spacer regions 508 into the second spacer regions 502 in the length of time that it takes the sample to travel down the reaction channel.

Assuming a receptor ligand assay system, test compounds pass into the device 500 and into reaction channel 510, where they are first combined with the receptor. The test compound/receptor, in the form of the subject material regions, are flowed along the reaction channel in the incubation zone 510a. Following this initial incubation, the test compound/receptor mix is combined with a labelled ligand (e.g., fluorescent ligand) whereupon this mixture flows along the second incubation region 510b of reaction channel 510. The lengths of the incubation regions and the flow rates of the system (determined by the potentials applied at each of the reservoirs 514, 516, 518, 520, 522, and at the terminus of sample channel 512) determine the time of incubation of the receptor with the fluorescent ligand and test compound. The ionic strengths of the solutions containing the receptors and fluorescent ligands, as well as the flow rates of material from the reservoirs housing these elements into the sample channel are selected so as to not interfere with the first and second spacer regions.

The isolated subject material regions containing receptor, fluorescent ligand and test compound are flowed along the reaction channel 510 by the application of potentials at, e.g., reservoirs 514, 516, 518 and at the terminus of sample channel 512. Potentials are also applied at reservoirs 520 and 522, at the opposite ends of separation channel 524, to match the potentials at the two ends of the transfer channel, so that the net flow across the transfer channel is zero. As the subject material region passes the intersection of reaction channel 510 and transfer channel 526, the potentials are allowed to float at reservoirs 518 and 522, whereupon the potentials applied at reservoirs 514, 516, 520, and at the terminus of sample channel 512, result in the subject material region being shunted through transfer channel 526 and into separation channel 524. Once in the separation channel, the original potentials are reapplied to all of the reservoirs to stop the net fluid flow through transfer channel 526. The diversion of the subject material can then be repeated with each subsequent subject material region. Within the separation channel, the subject material region is exposed to different conditions than those of the reaction channel. For example, a different flow rate may be used, capillary treatments may allow for separation of differentially charged or different sized species, and the like. In a preferred aspect, the subject material is shunted into the separation channel to place the subject material into a capillary filled with high ionic strength buffer, i.e., to remove the low ionic strength spacer regions, thereby allowing separation of the various sample components outside the confines of the original subject material region. For example, in the case of the above-described receptor/ligand screen, the receptor/ligand complex may have a different electrophoretic mobility from the ligand alone, in the transfer channel, thereby allowing more pronounced separation of the complex from the ligand, and its subsequent detection.

Such modifications have a wide variety of uses, particularly where it is desirable to separate reaction products following reaction, e.g., in cleavage reactions, fragmentation reactions, PCR reactions, and the like.

C. Serial in Parallel Assay Systems

Figure 3:
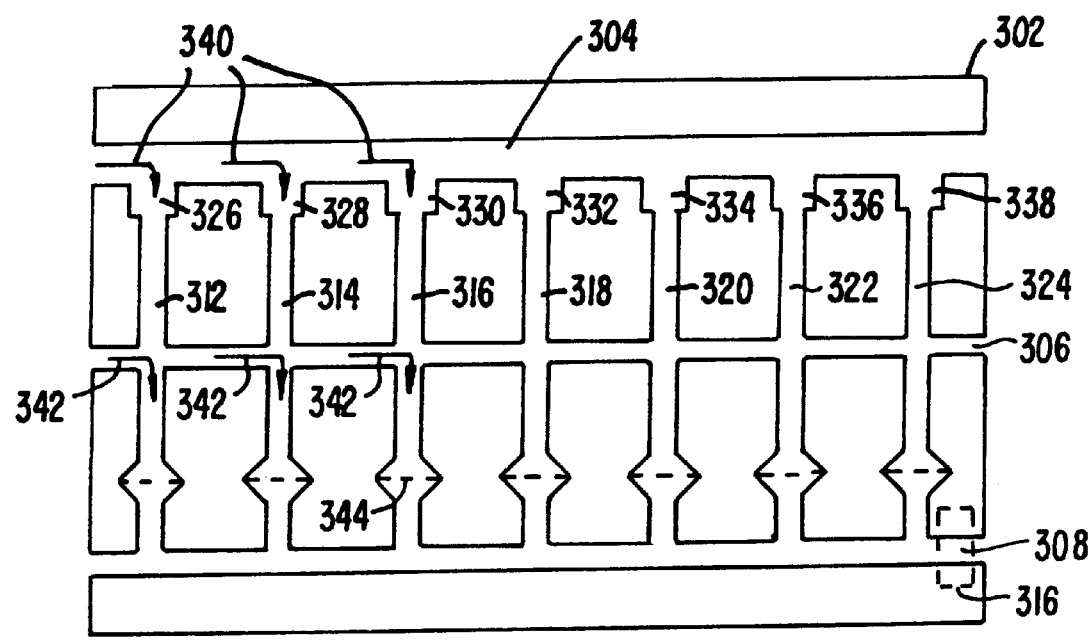
FIG. 3 is a schematic illustration of a "serial input parallel reaction" microlaboratory assay system in which compounds to be screened are serially introduced into the device but then screened in a parallel orientation within the device.

More complex systems can also be produced within the scope of the present invention. For example, a schematic illustration of one alternate embodiment employing a "serial input parallel reaction" geometry is shown in FIG. 3. As shown, the device 300 again includes a planar substrate 302 as described previously. Fabricated into the surface of the substrate 302 are a series of parallel reaction channels 312–324. Also shown are three transverse channels fluidly connected to each of these parallel reaction channels. The three transverse channels include a sample injection channel 304, an optional seeding channel 306 and a collection channel 308. Again, the substrate and channels are generally fabricated utilizing the materials and to the dimensions generally described above. Although shown and described in terms of a series of parallel channels, the reaction channels may also be fabricated in a variety of different orientations. For example, rather than providing a series of parallel channels fluidly connected to a single transverse channel, the channels are optionally fabricated connecting to and extending radially outward from a central reservoir, or are optionally arranged in some other non-parallel fashion. Additionally, although shown with three transverse channels, it will be recognized that fewer transverse channels are used where, e.g., the biochemical system components are predisposed within the device. Similarly, where desired, more transverse channels are optionally used to introduce further elements into a given assay screen. Accordingly, the serial-in- parallel devices of the present invention will typically include at least two and preferably three, four, five or more transverse channels. Similarly, although shown with 7 reaction channels, it will be readily appreciated that the microscale devices of the present invention will be capable of comprising more than 7 channels, depending upon the needs of the particular screen. In preferred aspects, the devices will include from 10 to about 500 reaction channels, and more preferably, from 20 to about 200 reaction channels.

This device may be particularly useful for screening test compounds serially injected into the device, but employing a parallel assay geometry, once the samples are introduced into the device, to allow for increased throughput.

In operation, test compounds in discrete subject material regions, are serially introduced into the device, separated as described above, and flowed along the transverse sample injection channel 304 until the separate subject material regions are adjacent the intersection of the sample channel 304 with the parallel reaction channels 310–324. As shown in FIGS. 4A–4F, the test compounds are optionally provided immobilized on individual beads. In those cases where the test compounds are immobilized on beads, the parallel channels are optionally fabricated to include bead resting wells 326–338 at the intersection of the reaction channels with the sample injection channel 304. Arrows 340 indicate the net fluid flow during this type of sample/bead injection. As individual beads settle into a resting well, fluid flow through that particular channel will be generally restricted. The next bead in the series following the unrestricted fluid flow, then flows to the next available resting well to settle in place.

Once in position adjacent to the intersection of the parallel reaction channel and the sample injection channel, the test compound is directed into its respective reaction channel by redirecting fluid flows down those channels. Again, in those instances where the test compound is immobilized on a bead, the immobilization will typically be via a cleavable linker group, e.g., a photolabile, acid or base labile linker group. Accordingly, the test compound will typically need to be released from the bead, e.g., by exposure to a releasing agent such as light, acid, base or the like prior to flowing the test compound down the reaction channel.

Within the parallel channel, the test compound will be contacted with the biochemical system for which an effector compound is being sought. As shown, the first component of the biochemical system is placed into the reaction channels using a similar technique to that described for the test compounds. In particular, the biochemical system is typically introduced via one or more transverse seeding channels 306. Arrows 342 illustrate the direction of fluid flow within the seeding channel 306. The biochemical system are optionally solution based, e.g., a continuously flowing enzyme/substrate or receptor-ligand mixture, like that described above, or as shown in FIGS. 4A–4F, may be a whole cell or bead based system, e.g., beads which have enzyme/substrate systems immobilized thereon.

In those instances where the biochemical system is incorporated in a particle, e.g., a cell or bead, the parallel channel may include a particle retention zone 344. Typically, such retention zones will include a particle sieving or filtration matrix, e.g., a porous gel or microstructure which retains particulate material but allows the free flow of fluids. Examples of microstructures for this filtration include, e.g., those described in U.S. Pat. No. 5,304,487, which is hereby incorporated by reference in its entirety for all purposes. As with the continuous system, fluid direction within the more complex systems may be generally controlled using microfabricated fluid direction structures, e.g., pumps and valves. However, as the systems grow more complex, such systems become largely unmanageable. Accordingly, electroosmotic systems, as described above, are generally preferred for controlling fluid in these more complex systems. Typically, such systems will incorporate electrodes within reservoirs disposed at the termini of the various transverse channels to control fluid flow thorough the device. In some aspects, it is desirable to include electrodes at the termini of all the various channels. This generally provides for more direct control, but also grows less manageable as systems grow more complex. In order to utilize fewer electrodes and thus reduce the potential complexity, it may often be desirable in parallel systems, e.g., where two fluids are desired to move at similar rates in parallel channels, to adjust the geometries of the various flow channels. In particular, as channel length increases, resistance along that channel will also increase. As such, flow lengths between electrodes should be designed to be substantially the same regardless of the parallel path chosen. This will generally prevent the generation of transverse electrical fields and thus promote equal flow in all parallel channels. To accomplish substantially the same resistance between the electrodes, one can alter the geometry of the channel structure to provide for the same channel length, and thus, the channel resistance, regardless of the path travelled. Alternatively, resistance of channels are optionally adjusted by varying the cross-sectional dimensions of the paths, thereby creating uniform resistance levels regardless of the path taken.

As the test compounds are drawn through their respective parallel reaction channels, they will contact the biochemical system in question. As described above, the particular biochemical system will typically include a flowable indicator system which indicates the relative functioning of that system, e.g., a soluble indicator such as chromogenic or fluorogenic substrate, labelled ligand, or the like, or a particle based signal, such as a precipitate or bead bound signalling group. The flowable indicator is then flowed through the respective parallel channel and into the collection channel 308 whereupon the signals from each of the parallel channels are flowed, in series, past the detection window, 116.

Figure 4A:
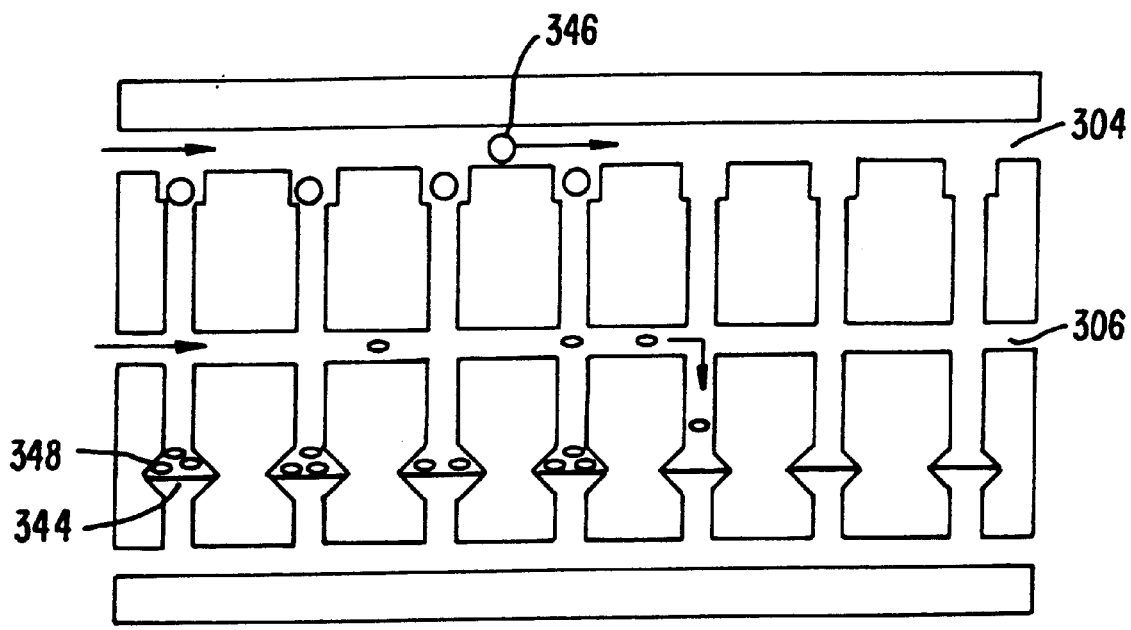
FIGS. 4A–4F show a schematic illustration of the operation of the device shown in FIG. 3, in screening a plurality of bead based test compounds.

FIGS. 4A–4F, with reference to FIG. 3, show a schematic illustration of the progression of the injection of test compounds and biochemical system components into the "serial input parallel reaction" device, exposure of the system to the test compounds, and flowing of the resulting signal out of the parallel reaction channels and past the detection window. In particular, FIG. 4A shows the introduction of test compounds immobilized on beads 346 through sample injection channel 304. Similarly, the biochemical system components 348 are introduced into the reaction channels 312–324 through seeding channel 306. Although shown as being introduced into the device along with the test compounds, as described above, the components of the model system to be screened are optionally incorporated into the reaction channels during manufacture. Again, such components are optionally provided in liquid form or in lyophilized form for increased shelf life of the particular screening device.

As shown, the biochemical system components are embodied in a cellular or particle based system, however, fluid components may also be used as described herein. As the particulate components flow into the reaction channels, they are optionally retained upon an optional particle retaining matrix 344, as described above.

Figure 4B:
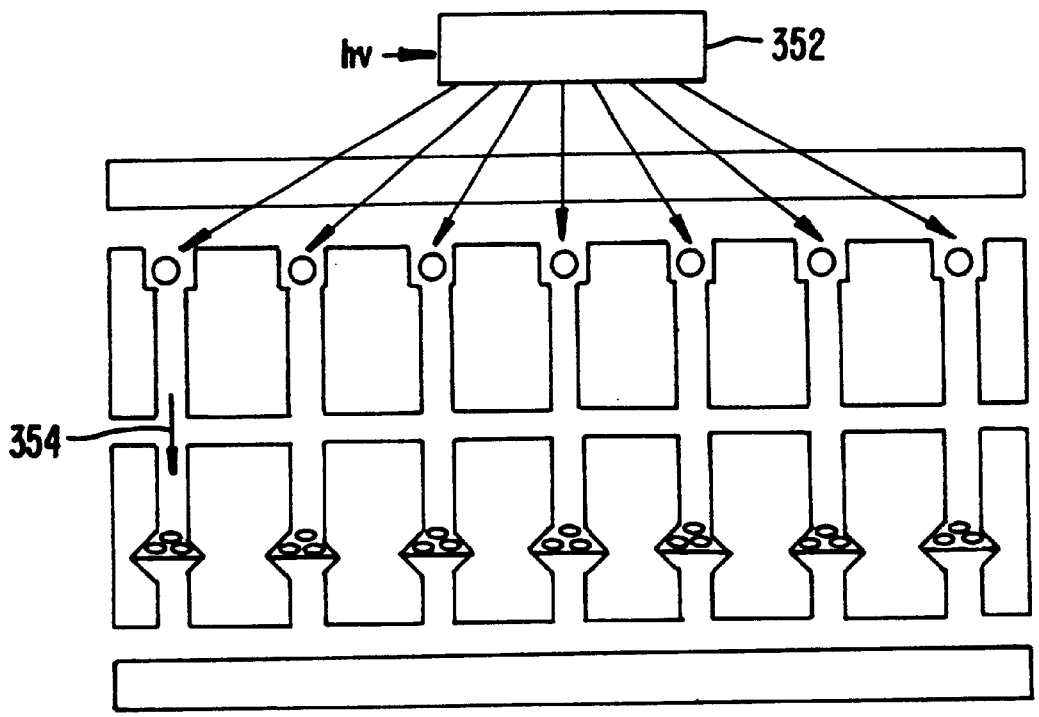

FIG. 4B illustrates the release of test compounds from the beads 346 by exposing the beads to a releasing agent. As shown, the beads are exposed to light from an appropriate light source 352, e.g., which is able to produce light in a wavelength sufficient to photolyze the linker group, thereby releasing compounds that are coupled to their respective beads via a photolabile linker group.

Figure 4C:
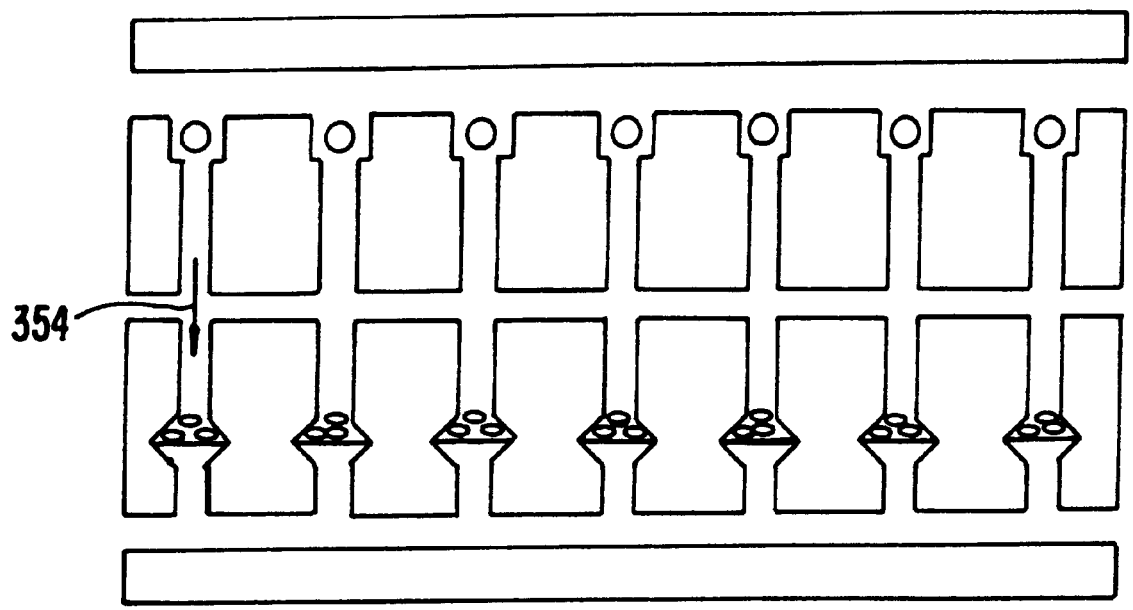
Figure 4D:
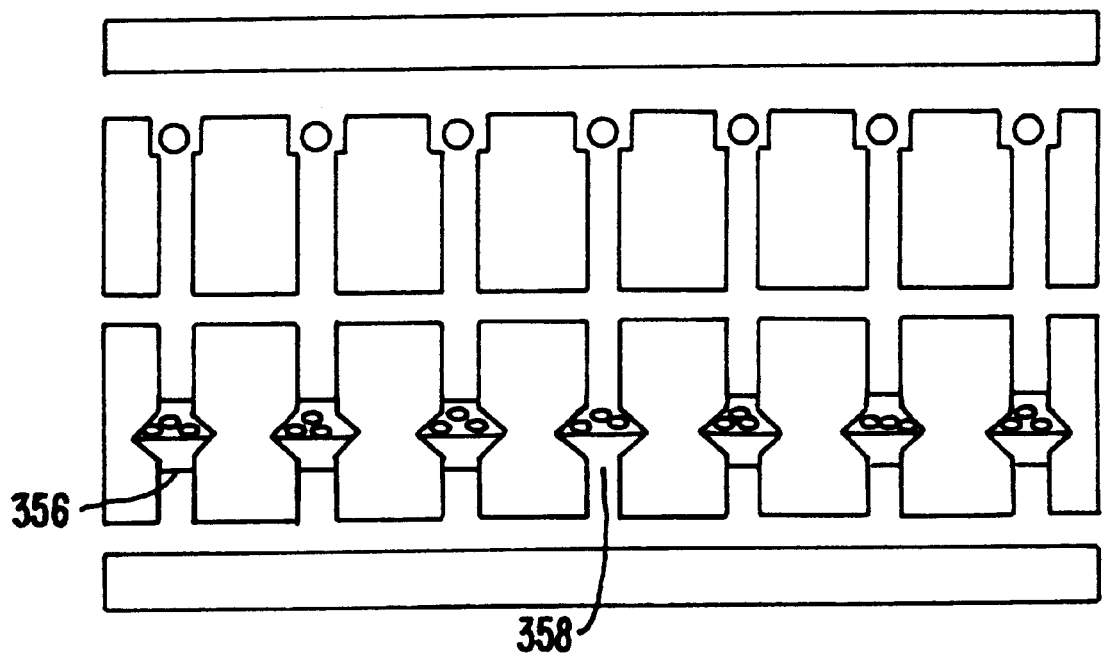

In FIG. 4C, the released test compounds are flowed into and along the parallel reaction channels as shown by arrows 354 until they contact the biochemical system components. The biochemical system components 348 are then allowed to perform their function, e.g., enzymatic reaction, receptor/ligand interaction, and the like, in the presence of the test compounds. Where the various components of the biochemical system are immobilized on a solid support, release of the components from their supports can provide the initiating event for the system. A soluble signal 356 which corresponds to the functioning of the biochemical system is then generated (FIG. 4D). As described previously, a variation in the level of signal produced is an indication that the particular test compound is an effector of the particular biochemical system. This is illustrated by the lighter shading of signal 358.

Figure 4E:
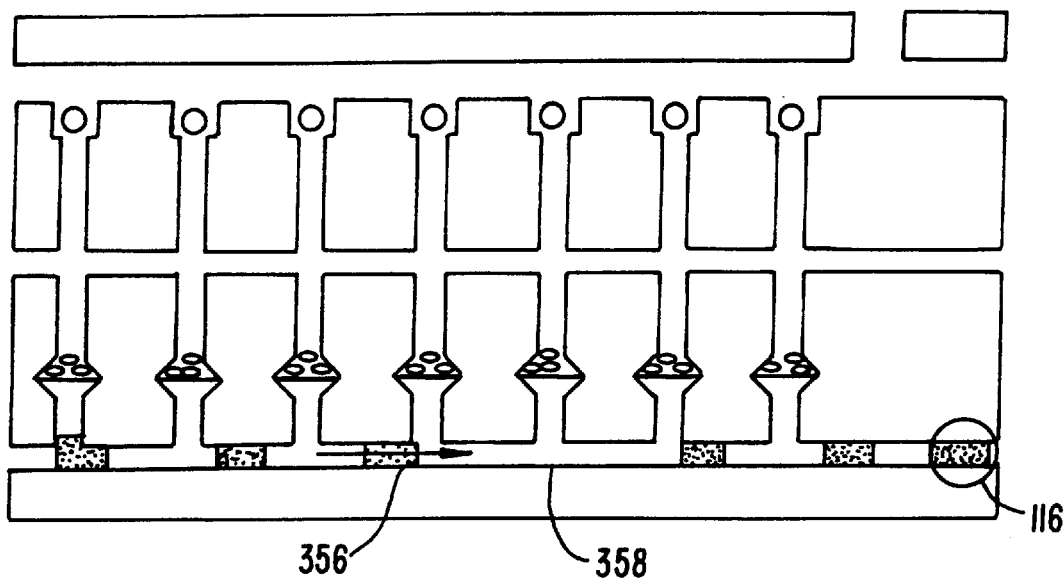
Figure 4F:
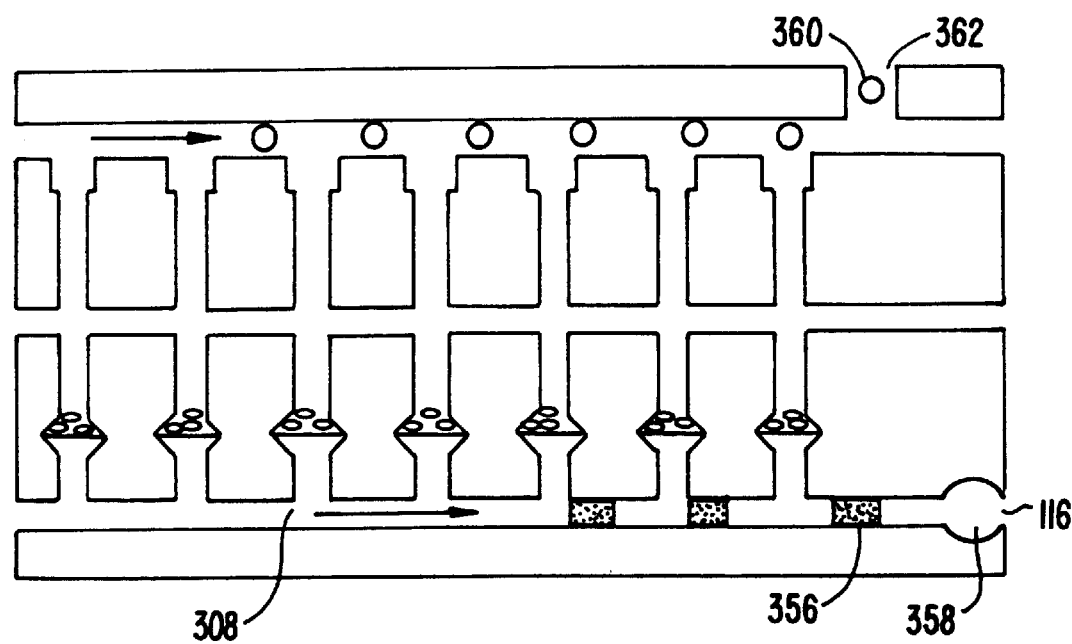

In FIGS. 4E and 4F, the soluble signal is then flowed out of reactions channels 312–324 into the detection channel 308, and along the detection channel past the detection window 116.

Again, a detection system as described above, located adjacent the detection window will monitor the signal levels. In some embodiments, the beads which bore the test compounds are optionally recovered to identify the test compounds which were present thereon. This is typically accomplished by incorporation of a tagging group during the synthesis of the test compound on the bead. As shown, spent bead 360, i.e., from which a test compound has been released, is optionally transported out of the channel structure through port 362 for identification of the test compound that had been coupled to it. Such identification are optionally accomplished outside of the device by directing the bead to a fraction collector, whereupon the test compounds present on the beads are optionally identified, either through identification of a tagging group, or through identification of residual compounds. Incorporation of tagging groups in combinatorial chemistry methods has been previously described using encrypted nucleotide sequences or chlorinated/fluorinated aromatic compounds as tagging groups. See, e.g., Published PCT Application No. WO 95/12608. Alternatively, the beads are optionally transported to a separate assay system within the device itself whereupon the identification is carried out.

Figure 6A:
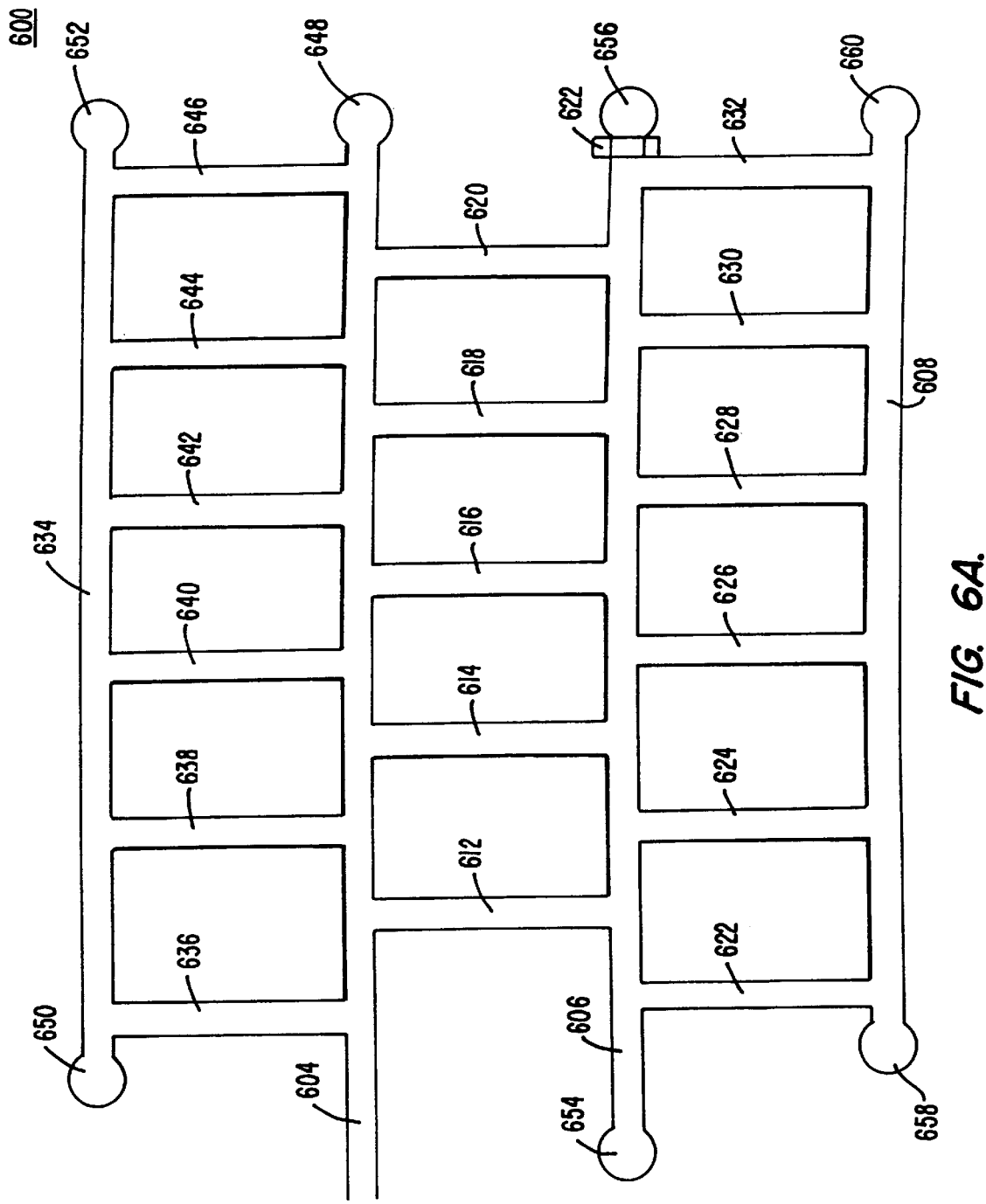
FIG. 6A shows a schematic illustration of a serial input parallel reaction device for use with fluid based test compounds.

FIG. 6A shows an alternate embodiment of a "serial input parallel reaction" device which can be used for fluid based as opposed to bead based systems. As shown the device 600 generally incorporates at least two transverse channels as were shown in FIGS. 3 and 4, namely, sample injection channel 604 and detection channel 606. These transverse channels are interconnected by the series of parallel channels 612–620 which connect sample channel 604 to detection channel 606.

The device shown also includes an additional set of channels for directing the flow of fluid test compounds into the reaction channels. In particular, an additional transverse pumping channel 634 is fluidly connected to sample channel 604 via a series of parallel pumping channels 636–646. The pumping channel includes reservoirs 650 and 652 at its termini. The intersections of parallel channels 636–646 are staggered from the intersections of parallel channels 612–620 with sample channel 604, e.g., half way between. Similarly, transverse pumping channel 608 is connected to detection channel 606 via parallel pumping channels 622–632. Again, the intersections of parallel pumping channels 622–632 with detection channel 606 are staggered from the intersections of reaction channels 612–620 with the detection channel 606.

Figure 6B:
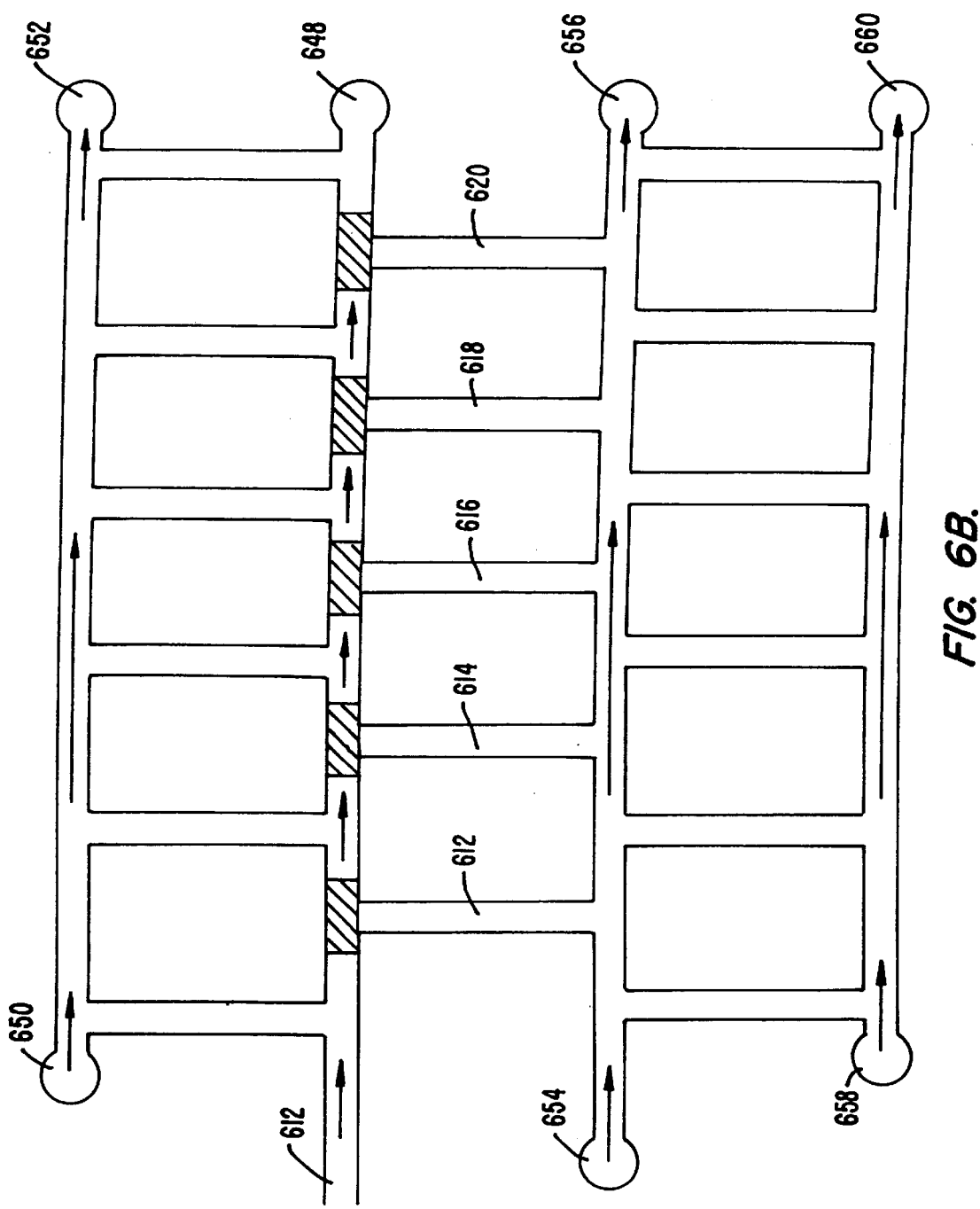
FIGS. 6B and 6C show a schematic illustration of fluid flow patterns within the device shown in FIG. 6A.
Figure 6C:
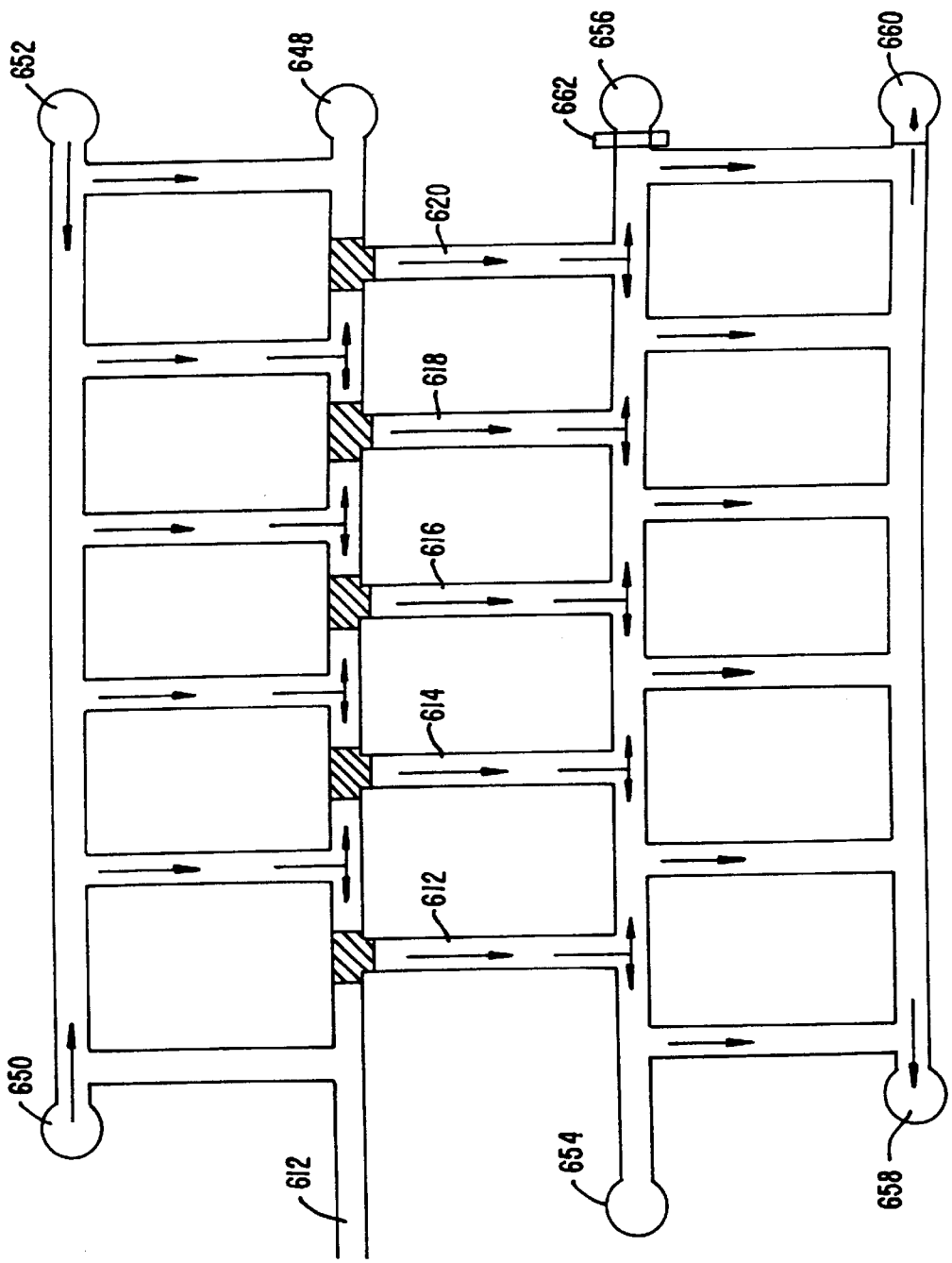

A schematic illustration of the operation of this system is shown in FIGS. 6B–6C. As shown, a series of test compounds, physically isolated from each other in separate subject material regions, are introduced into sample channel 604 using the methods described previously. For electroosmotic systems, potentials are applied at the terminus of sample channel 604, as well as reservoir 648. Potentials are also applied at reservoirs 650:652, 654:656, and 658:660. This results in a fluid flow along the transverse channels 634, 604, 606 and 608, as illustrated by the arrows, and a zero net flow through the parallel channel arrays interconnecting these transverse channels, as shown in FIG. 6B. Once the subject material regions containing the test compounds are aligned with parallel reaction channels 612–620, connecting sample channel 604 to detection channel 606, as shown by the shaded areas in FIG. 6B, flow is stopped in all transverse directions by removing the potentials applied to the reservoirs at the ends of these channels. As described above, the geometry of the channels can be varied to maximize the use of space on the substrate. For example, where the sample channel is straight, the distance between reaction channels (and thus, the number of parallel reactions that can be carried out in a size limited substrate) is dictated by the distance between subject material regions. These restrictions, however, can be eliminated through the inclusion of altered channel geometries. For example, in some aspects, the length of a first and second spacer regions can be accommodated by a serpentine, square-wave, saw tooth or other reciprocating channel geometry. This allows packing a maximum number of reaction channels onto the limited area of the substrate surface.

Once aligned with the parallel reaction channels, the sample, or subject material, is then moved into the parallel reaction channels 612–620 by applying a first potential to reservoirs 650 and 652, while applying a second potential to reservoirs 658 and 660, whereby fluid flow through parallel pumping channels 636–646 forces the subject material into parallel reaction channels 612–620, as shown in FIG. 6C.

During this process, no potential is applied at reservoirs 648, 654, 656, or the terminus of sample channel 604. Parallel channels 636–646 and 622–632 are generally adjusted in length such that the total channel length, and thus the level of resistance, from reservoirs 650 and 652 to channel 604 and from reservoirs 658 and 660 to channel 606, for any path taken will be the same. Resistance can generally be adjusted by adjusting channel length or width. For example, channels can be lengthened by including folding or serpentine geometries. Although not shown as such, to accomplish this same channel length, channels 636 and 646 would be the longest and 640 and 642 the shortest, to create symmetric flow, thereby forcing the samples into the channels. As can be seen, during flowing of the samples through channels 612–620, the resistance within these channels will be the same, as the individual channel length is the same.

Following the reaction to be screened, the subject material region/signal element is moved into detection channel 606 by applying a potential from reservoirs 650 and 652 to reservoirs 658 and 660, while the potentials at the remaining reservoirs are allowed to float. The subject material regions/ signal are then serially moved past the detection window/ detector 662 by applying potentials to reservoirs 654 and 656, while applying appropriate potentials at the termini of the other transverse channels to prevent any flow along the various parallel channels.

Although shown with channels which intersect at right angles, it will be appreciated that other geometries are also appropriate for serial input parallel reactions. For example, U.S. Ser. No. 08/835,101, filed Apr. 4, 1997, describes advantages to parabolic geometries and channels which vary in width for control of fluid flow. In brief, fluid flow in electroosmotic systems is controlled by and therefore related to current flow between electrodes. Resistance in the fluid channels varies as a function of path length and width, and thus, different length channels have different resistances. If this differential in resistance is not corrected for, it results in the creation of transverse electrical fields which can inhibit the ability of the devices to direct fluid flow to particular regions. The current, and thus the fluid flow, follows the path of least resistance, e.g., the shortest path. While this problem of transverse electrical fields is alleviated through the use of separate electrical systems, i.e., separate electrodes, at the termini of each and every parallel channel, production of devices incorporating all of these electrodes, and control systems for controlling the electrical potential applied at each of these electrodes can be complex, particularly where one is dealing with hundreds to thousands of parallel channels in a single small scale device, e.g., 1–2 $cm^2$. Accordingly, the present invention provides microfluidic devices for affecting serial to parallel conversion, by ensuring that current flow through each of a plurality of parallel channels is at an appropriate level to ensure a desired flow pattern through those channels or channel networks. A number of methods and substrate/channel designs for accomplishing these goals are appropriate.

In one example of parabolic geometry for the channels in an apparatus of the invention, the substrate includes a main channel. A series of parallel channels terminate in a main channel. The opposite termini of these parallel channels are connected to parabolic channels. Electrodes are disposed at the termini of these parabolic channels. The current flow in each of the parallel channels is maintained constant or equivalent, by adjusting the length of the parallel channels, resulting in a parabolic channel structure connecting each of the parallel channels to its respective electrodes. The voltage drop within the parabolic channel between the parallel channels is maintained constant by adjusting the channel width to accommodate variations in the channel current resulting from the parallel current paths created by these parallel channels. The parabolic design of the channels, in combination with their tapering structures, results in the resistance along all of the parallel channels being equal, resulting in an equal fluid flow, regardless of the path chosen. Generally, determining the dimensions of channels to ensure that the resistances among the channels are controlled as desired, may be carried out by well known methods, and generally depends upon factors such as the make-up of the fluids being moved through the substrates.

Although generally described in terms of screening assays for identification of compounds which affect a particular interaction, based upon the present disclosure, it will be readily appreciated that the above described microlaboratory systems may also be used to screen for compounds which specifically interact with a component of a biochemical system without necessarily affecting an interaction between that component and another element of the biochemical system. Such compounds typically include binding compounds which may generally be used in, e.g., diagnostic and therapeutic applications as targeting groups for therapeutics or marker groups, i.e. radionuclides, dyes and the like. For example, these systems are optionally used to screen test compounds for the ability to bind to a given component of a biochemical system.

II. Microlaboratory System

Although generally described in terms of individual discrete devices, for ease of operation, the systems described will typically be a part of a larger system which can monitor and control the functioning of the devices, either on an individual basis, or in parallel, multi-device screens. An example of such a system is shown in FIG. 7.

Figure 7:
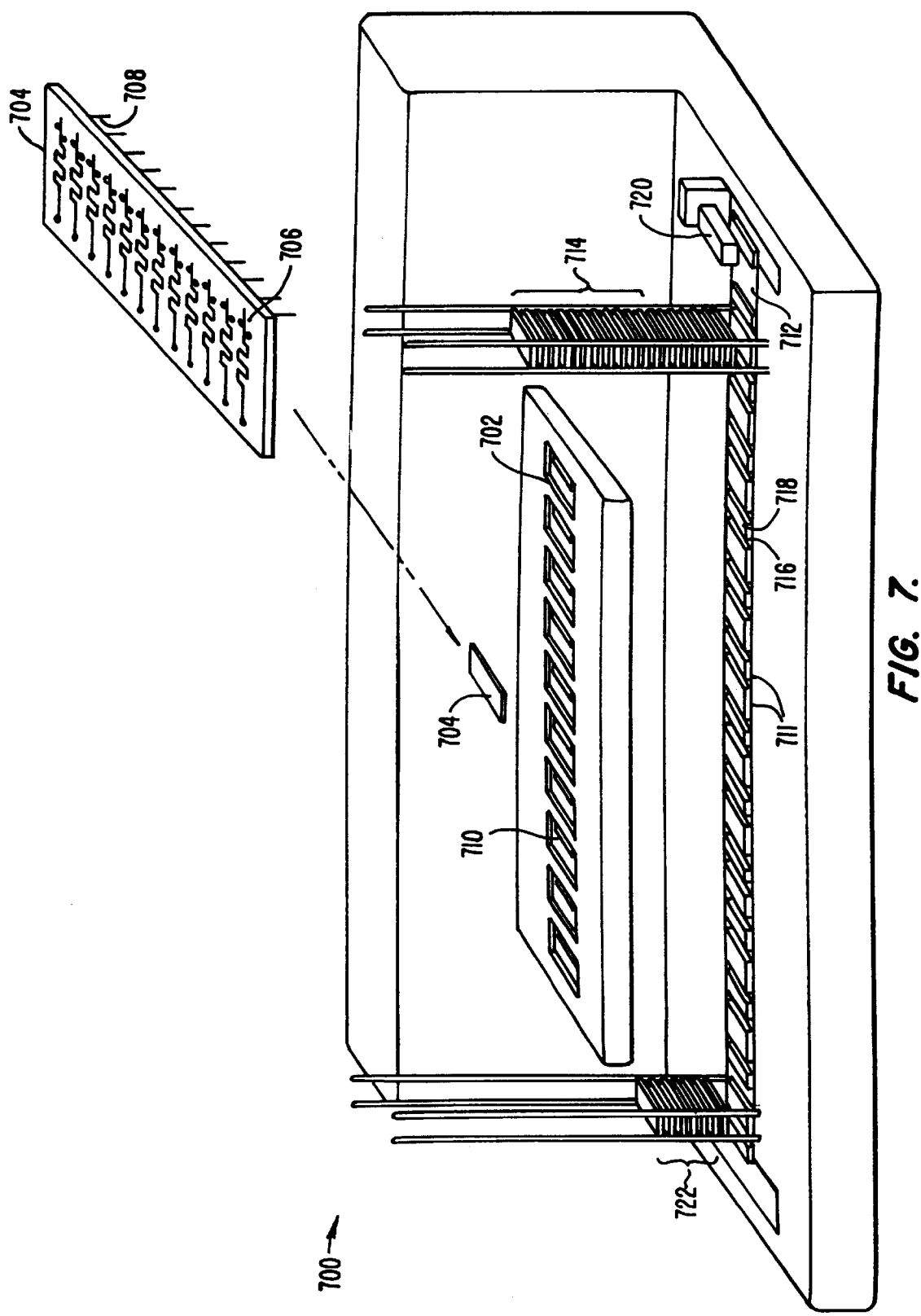
FIG. 7 shows a schematic illustration of one embodiment of an overall assay systems which employs multiple microlaboratory devices labeled as "LabChips™" for screening test compounds.

As shown in FIG. 7, the system may include a test compound processing system 700. The system shown includes a platform 702 which can hold a number of separate assay chips or devices 704. As shown, each chip includes a number of discrete assay channels 706, each having a separate interface 708, e.g., pipettor, for introducing test compounds into the device. These interfaces are used to sip test compounds into the device, separated by sipping first and second spacer fluids, into the device. In the system shown, the interfaces of the chip are inserted through an opening 710 in the bottom of the platform 702, which is capable of being raised and lowered to place the interfaces in contact with test compounds or wash/first spacer fluids/ second spacer fluids, which are contained in, e.g., multiwell micro plates 711, positioned below the platform, e.g., on a conveyor system 712. In operation, multiwell plates containing large numbers of different test compounds are stacked 714 at one end of the conveyor system. The plates are placed upon the conveyor separated by appropriate buffer reservoirs 716 and 718, which may be filled by buffer system 720. The plates are stepped down the conveyor and the test compounds are sampled into the chips, interspersed by appropriate spacer fluid regions. After loading the test compounds into the chips, the multiwell plates are then collected or stacked 722 at the opposite end of the system. The overall control system includes a number of individual microlaboratory systems or devices, e.g., as shown in FIG. 7. Each device is connected to a computer system which is appropriately programmed to control fluid flow and direction within the various chips, and to monitor, record and analyze data resulting from the screening assays that are performed by the various devices. The devices will typically be connected to the computer through an intermediate adapter module which provides an interface between the computer and the individual devices for implementing operational instructions from the computer to the devices, and for reporting data from the devices to the computer. For example, the adapter will generally include appropriate connections to corresponding elements on each device, e.g., electrical leads connected to the reservoir based electrodes that are used for electroosmotic fluid flow, power inputs and data outputs for detection systems, either electrical or fiberoptic, and data relays for other sensor elements incorporated into the devices. The adapter device may also provide environmental control over the individual devices where such control is necessary, e.g., maintaining the individual devices at optimal temperatures for performing the particular screening assays.

As shown, each device is also equipped with appropriate fluid interfaces, e.g., micropipettors, for introducing test compounds into the individual devices. The devices may readily be attached to robotic systems which allow test compounds to be sampled from a number of multiwell plates that are moved along a conveyor system. Intervening spacer fluid regions can also be introduced via a spacer solution reservoir.

III. Fluid Electrode Interface to Prevent Degradation of Chemical Species in a Microchip When pumping fluids or other materials electroosmotically or electrophoretically through an apparatus of the invention, chemical species in the fluid can be degraded if high voltages or currents are applied, or if voltages are applied for a long period of time. Designs which retard movement of chemical species from the electrode to a channel entrance or retard the movement of chemical species to the electrode improve performance of chemical assays by reducing unwanted degradation of chemical species within the sample. These designs are particularly preferred in assay systems where voltages are applied for long periods, e.g., several hours to several days.

Electrode designs which reduce degradation of chemical species in the assays of the invention are illustrated by consideration of FIG. 12, panels A–G. The designs retard the moving of chemical species from the electrode to the channel entrance or retard the movement of chemical species to the electrode improve performance of chemical assays. FIG. 12A shows a typical electrode design, in which electrode 1211 is partially submerged in reservoir 1215 fluidly connected to fluid channel 1217.

Figure 12A:
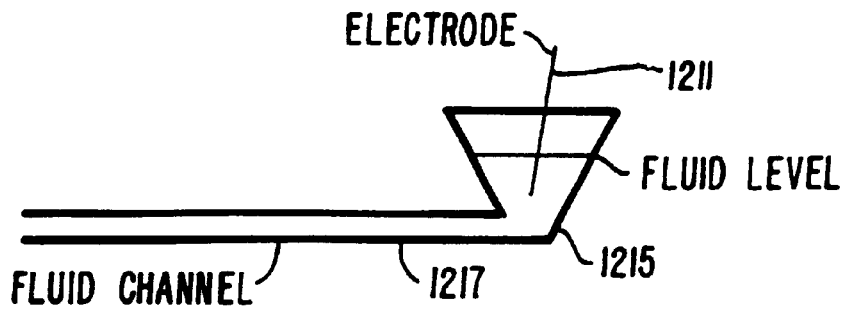
FIG. 12, panels A–G schematically illustrate electrodes used in apparatuses of the invention.
Figure 12B:
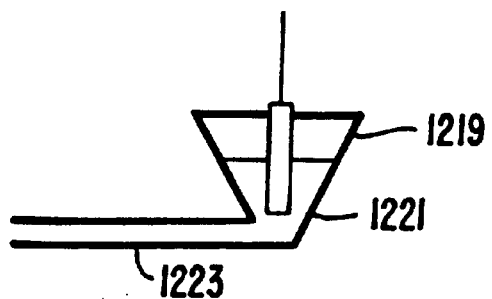

In comparison, FIG. 12B utilizes a salt bridge between electrode with frit 1219 and fluid reservoir 1221 fluidly connected to fluid channel 1223.

Figure 12C:
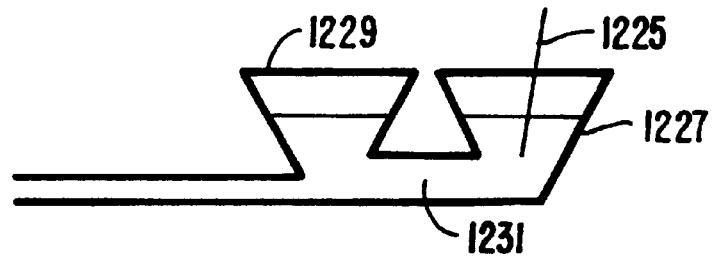

FIG. 12C reduces degradation of chemical species by providing electrode 1225 submersed in first fluid reservoir 1227 fluidly connected to second fluid reservoir 1229 by large channel 1231 which limits diffusion, but has a low electroosmotic flow.

Figure 12D:
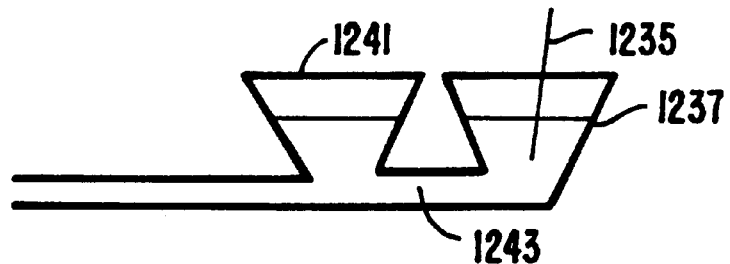

FIG. 12D provides a similar two part reservoir, in which electrode 1235 is submersed in first fluid reservoir 1237 fluidly connected to second fluid reservoir 1241 by small channel 1243 which is treated to reduce or eliminate electroosmotic flow.

Figure 12E:
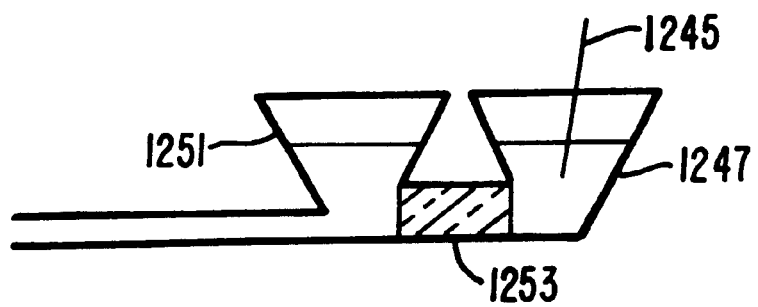

FIG. 12E provides another similar two part reservoir, in which electrode 1245 is submersed in first fluid reservoir 1247 fluidly connected to second fluid reservoir 1251 by channel 1253. Channel 1253 is filled with a material such as gel, Agar, glass beads or other matrix material for reducing electroosmotic flow.

Figure 12F:
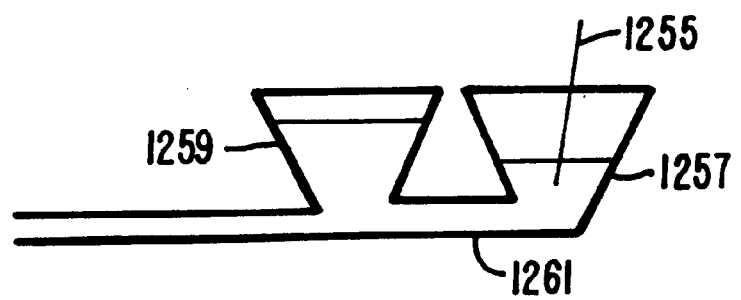

FIG. 12F provides a variant two part reservoir system, in which electrode 1255 is submersed in first fluid reservoir 1257 fluidly connected to second fluid reservoir 1259 by channel 1261. The fluid level in second fluid reservoir 1259 is higher than the fluid level in first fluid reservoir 1257, which forces fluid towards electrode 1255.

Figure 12G:
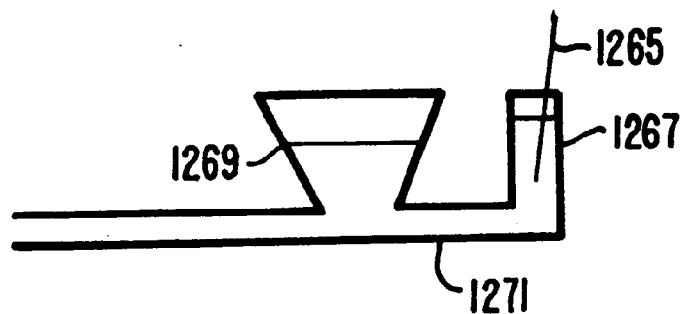

FIG. 12G provides a second variant two part reservoir, in which electrode 1265 is submersed in first fluid reservoir 1267 fluidly connected to second fluid reservoir 1269 by channel 1271. The diameter on first fluid reservoir 1267 is small enough that capillary forces draw fluid into first fluid reservoir 1267.

Modifications can be made to the method and apparatus as hereinbefore described without departing from the spirit or scope of the invention as claimed, and the invention can be put to a number of different uses, including:

The use of a microfluidic system containing at least a first substrate having a first channel and a second channel intersecting said first channel, at least one of said channels having at least one cross-sectional dimension in a range from 0.1 to 500 $\mu$m, in order to test the effect of each of a plurality of test compounds on a biochemical system.

The use of a microfluidic system as hereinbefore described, wherein said biochemical system flows through one of said channels substantially continuously, enabling sequential testing of said plurality of test compounds.

The use of a microfluidic system as hereinbefore described, wherein the provision of a plurality of reaction channels in said first substrate enables parallel exposure of a plurality of test compounds to at least one biochemical system.

The use of a microfluidic system as hereinbefore described, wherein each test compound is physically isolated from adjacent test compounds.

The use of a substrate carrying intersecting channels in screening test materials for effect on a biochemical system by flowing said test materials and biochemical system together using said channels.

The use of a substrate as hereinbefore described, wherein at least one of said channels has at least one cross-sectional dimension of range 0.1 to 500 $\mu$m.

An assay utilizing a use of any one of the microfluidic systems or substrates hereinbefore described.

The invention provides, inter alia, an apparatus for detecting an effect of a test compound on a biochemical system, comprising a substrate having at least one surface with a plurality of reaction channels fabricated into the surface. Apparatus as hereinbefore described, having at least two transverse channels fabricated into the surface, wherein each of the plurality of reaction channels is fluidly connected to a first of the at least two transverse channels at a first point in each of the reaction channels, and fluidly connected to a second transverse channel at a second point in each of the reaction channels and an assay apparatus including an apparatus as hereinbefore described are also provided.

EXAMPLE

The following examples are provided by way of illustration only and not by way of limitation. Those of skill will readily recognize a variety of noncritical parameters which can be changed or modified to yield essentially similar results.

Example 1

Enzyme Inhibitor Screen

Figure 8:
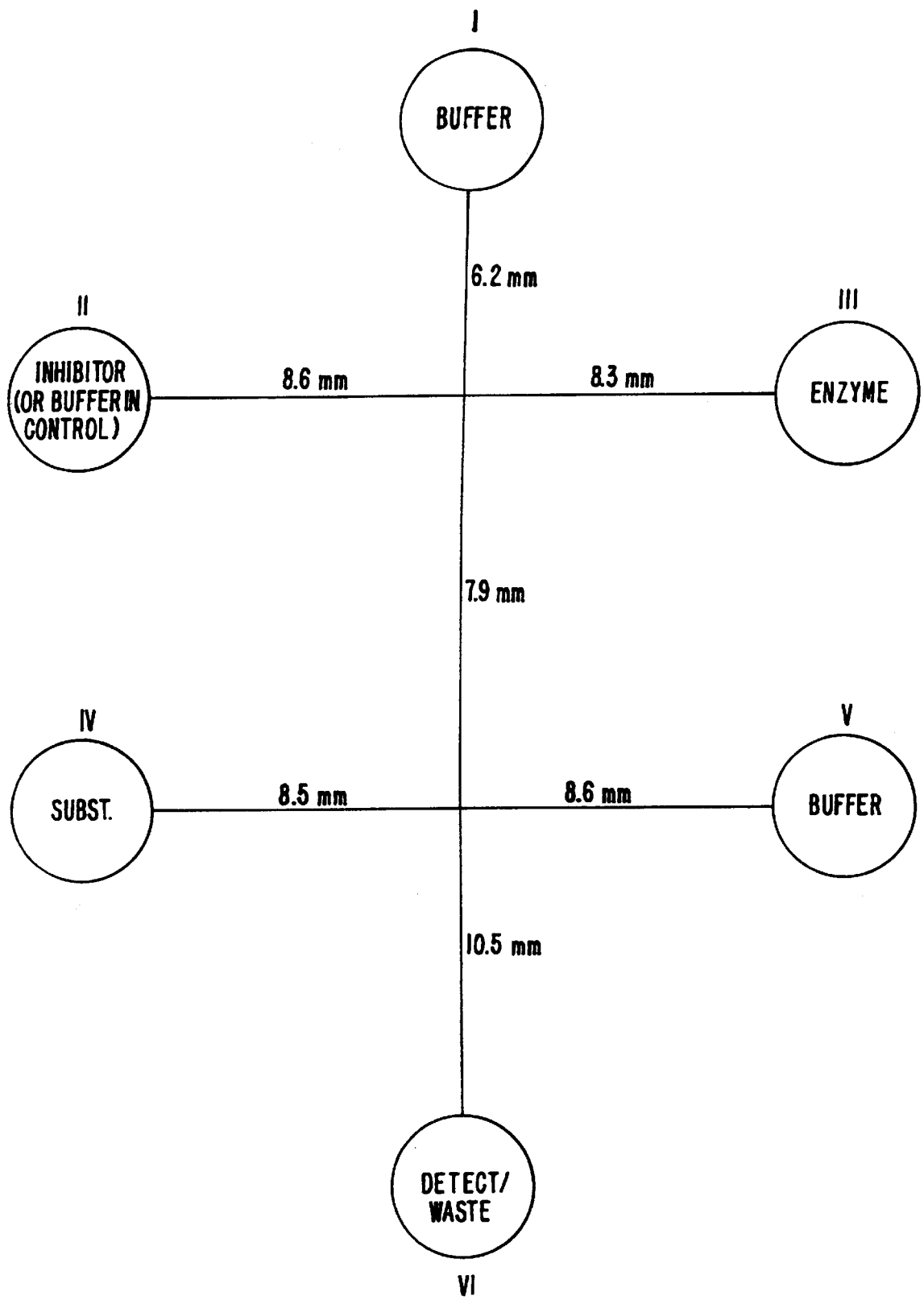
FIG. 8 is a schematic illustration of a chip layout used for a continuous-flow assay screening system.

The efficacy of performing an enzyme inhibition assay screen was demonstrated in a planar chip format. A 6-port planar chip was employed having the layout shown in FIG. 8. The numbers adjacent the channels represent the lengths of each channel in millimeters. Two voltage states were applied to the ports of the chip. The first state (State 1) resulted in flowing of enzyme with buffer from the top buffer well into the main channel. The second voltage state (State 2) resulted in the interruption of the flow of buffer from the top well, and the introduction of inhibitor from the inhibitor well, into the main channel along with the enzyme. A control experiment was also run in which buffer was placed into the inhibitor well.

Applied voltages at each port for each of the two applied voltage states were as follows:

|  | State 1 | State 2 |
|---|---|---|
| Top Buffer Well (I) | 1831 | 1498 |
| Inhibitor Well (II) | 1498 | 1900 |
| Enzyme Well (III) | 1891 | 1891 |
| Substrate Well (IV) | 1442 | 1442 |
| Bottom Buffer Well (V) | 1442 | 1442 |
| Detect./Waste Well (VI) | 0 | 0 |

To demonstrate the efficacy of the system, an assay was designed to screen inhibitors of β-galactosidase using the following enzyme/substrate/inhibitor reagents:

Enzyme: β-Galactosidase (180 U/ml in 50 mM Tris/300 μg/ml BSA

Substrate: Fluorescein-digalactoside (FDG) 400 μM

Inhibitor: IPTG, 200 mM

Buffer: 20 mM Tris, pH 8.5

Figure 9A:
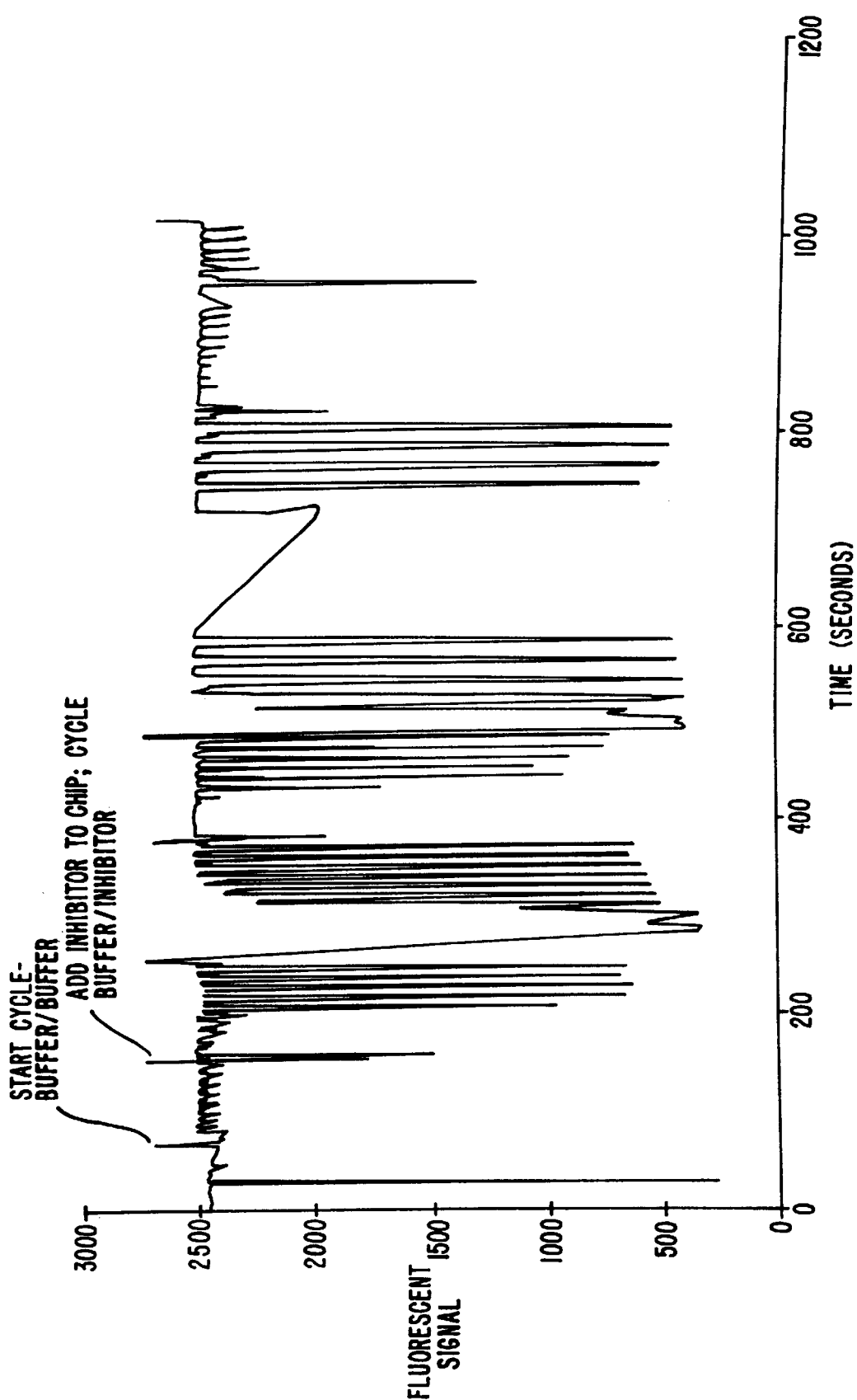
FIG. 9A shows fluorescence data from a test screen which periodically introduced a known inhibitor (IPTG) into a β-galactosidase assay system in a chip format.
Figure 9B:
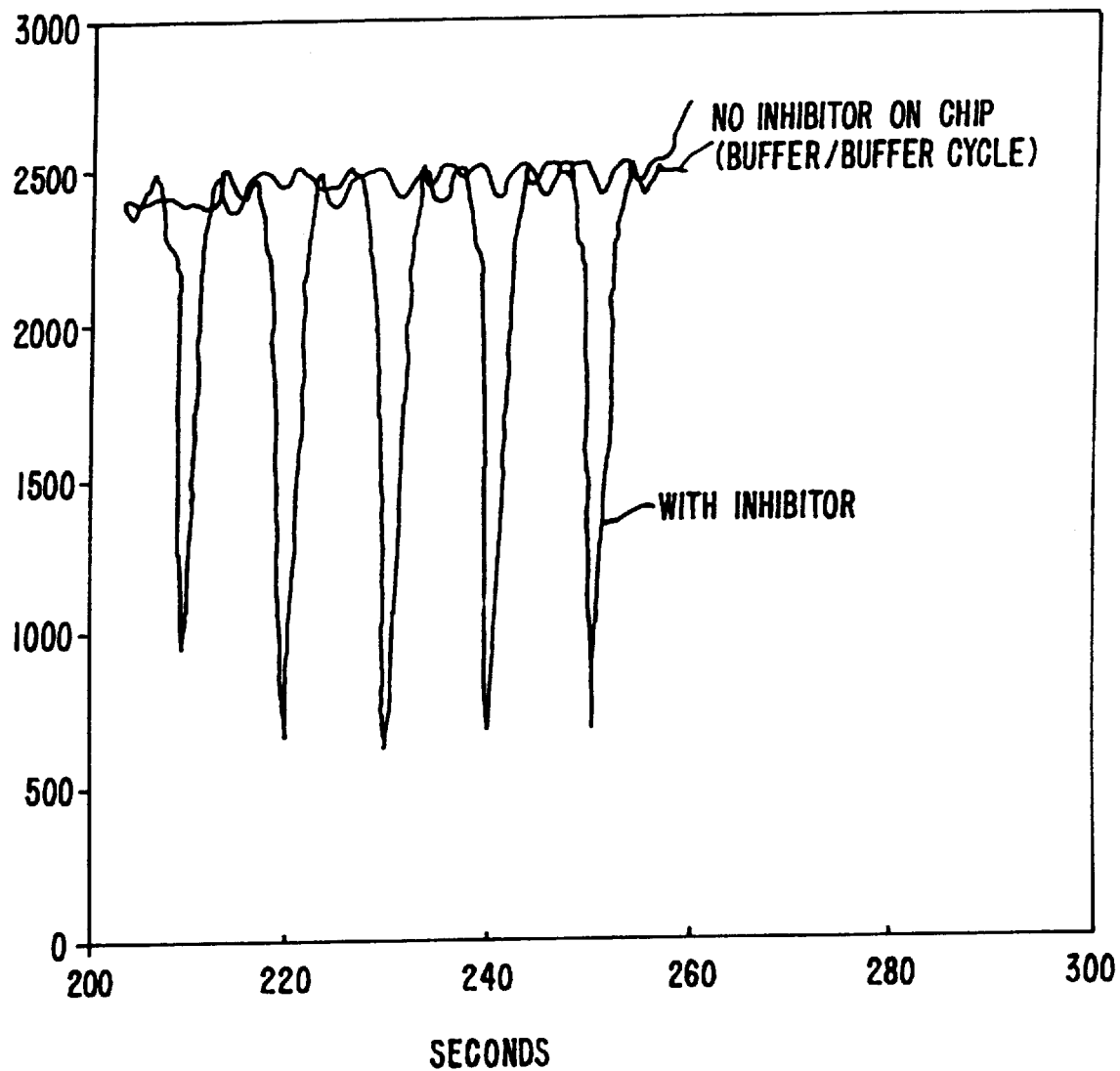
FIG. 9B shows a superposition of two data segments from FIG. 9A, directly comparing the inhibitor data with control (buffer) data.

Enzyme and substrate were continually pumped through the main channel from their respective ports under both voltage states. Inhibitor or Buffer were delivered into the main channel alternately from their respective wells by alternating between voltage state 1 and voltage state 2. When no inhibitor was present at the detection end of the main channel, a base line level of fluorescent product was produced. Upon introduction of inhibitor, the fluorescent signal was greatly reduced, indicating inhibition of the enzyme/substrate interaction. Fluorescent data obtained from the alternating delivery of inhibitor and buffer into the main channel is shown in FIG. 9A. FIG. 9B a superposition of the two data segments from FIG. 9A, directly comparing the inhibitor data with control (buffer) data. The control shows only a minor fluctuation in the fluorescent signal that apparently resulted from a dilution of the enzyme substrate mixture, whereas the inhibitor screen shows a substantial reduction in the fluorescent signal, indicating clear inhibition.

Example 2

Screening of Multiple Test Compounds

Figure 10:
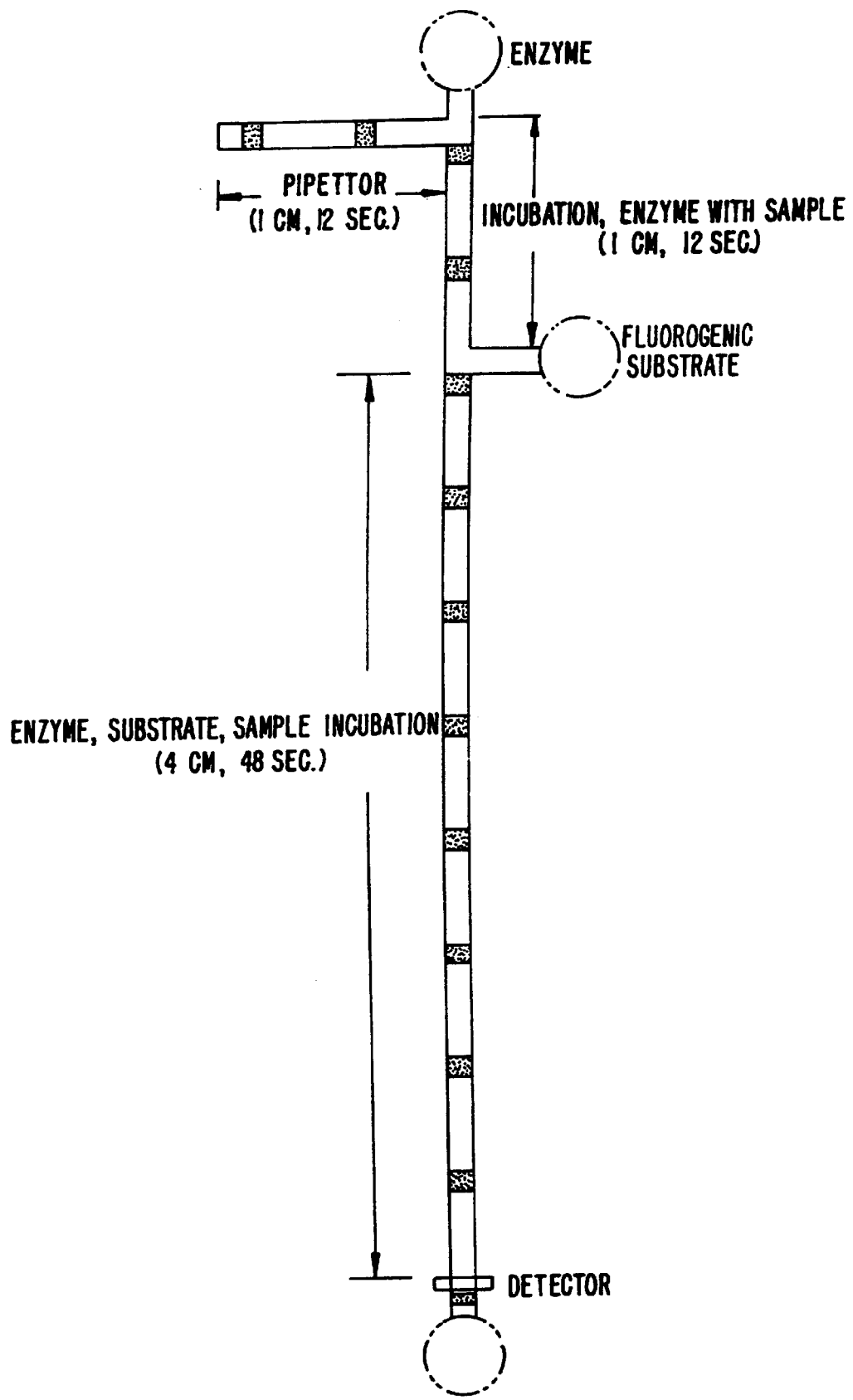
FIG. 10 illustrates the operating parameters of a fluid flow system on a small chip device for performing enzyme inhibitor screening.

An assay screen is performed to identify inhibitors of an enzymatic reaction. A schematic of the chip to be used is shown in FIG. 10. The chip has a reaction channel 5 cm in length which includes a 1 cm incubation zone and a 4 cm reaction zone. The reservoir at the beginning of the sample channel is filled with enzyme solution and the side reservoir is filled with the fluorogenic substrate. Each of the enzyme and substrate are diluted to provide for a steady state signal in the linear signal range for the assay system, at the detector. Potentials are applied at each of the reservoirs (sample source, enzyme, substrate and waste) to achieve an applied field of 200 V/cm. This applied field produces a flow rate of 2 mm/second. During passage of a given sample through the chip, there will generally be a diffusive broadening of the sample. For example, in the case of a small molecule sample, e.g., 1 mM benzoic acid diffusive broadening of approximately 0.38 mm and an electrophoretic shift of 0.4 mm is seen.

Figure 11:
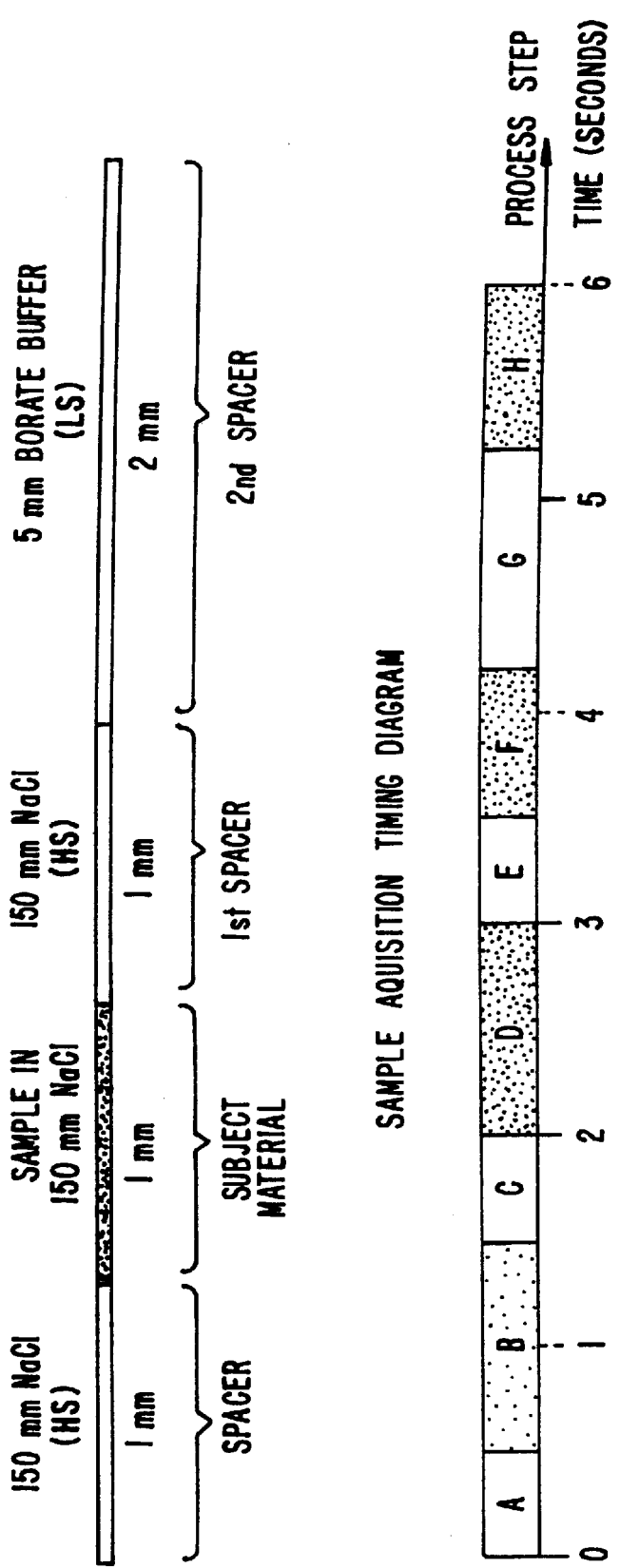
FIG. 11 shows a schematic illustration of timing for sample/spacer loading in a microfluidic device channel.

Subject material regions containing test compounds in 150 mM NaCl are introduced into the sample channel separated by first spacer regions of 150 mM NaCl and second spacer regions of 5 mM borate buffer. Once introduced into the sample channel shown, the subject material region requires 12 seconds to travel the length of the sample channel and reach the incubation zone of the reaction channel. This is a result of the flow rate of 2 mm/sec, allowing for 1 second for moving the sample pipettor from the sample to the spacer compounds. Allowing for these interruptions, the net flow rate is 0.68 mm/sec. Another 12 seconds is required for the enzyme/test compound mixture to travel through the incubation zone to the intersection with the substrate channel where substrate is continuously flowing into the reaction zone of the reaction channel. Each subject material region containing the test compounds then requires 48 seconds to travel the length of the reaction zone and past the fluorescence detector. A schematic of timing for subject material region/spacer region loading is shown in FIG. 11. The top panel shows the subject material/first spacer region/second spacer region distribution within a channel, whereas the lower panel shows the timing required for loading the channel. As shown, the schematic includes the loading (sipping) of high salt (HS) first spacer fluid ("A"), moving the pipettor to the sample or subject material ("B"), sipping the sample or subject material ("C"), moving the pipettor to the high salt first spacer fluid ("D") sipping the first spacer fluid ("E"), moving the pipettor to the low salt (LS) or second spacer fluid ("F"), sipping the second spacer fluid ("G") and returning to the first spacer fluid ("H"). The process is then repeated for each additional test compound.

A constant base fluorescent signal is established at the detector in the absence of test compounds. Upon introduction of the test compounds, a decrease in fluorescence is seen similar to that shown in FIGS. 9A and 9B, which, based upon time delays, corresponds to a specific individual test compound. This test compound is tentatively identified as an inhibitor of the enzyme, and further testing is conducted to confirm this and quantitate the efficacy of this inhibitor.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

What is claimed is:

1. An apparatus for analyzing a plurality of test compounds, said apparatus comprising:

(i) a platform configured to receive at least one microfluidic device in a microfluidic device holding region in or on the platform;

(ii) a multiwell plate stacking region for stacking a plurality of multiwell plates;

(iii) a plate conveyor system which, during operation of the apparatus, transports at least one multiwell plate from the multiwell plate stacking region to a position proximal to the microfluidic device holding region of the platform, thereby facilitating contact between the at least one multiwell plate and the at least one microfluidic device during operation of the apparatus; and, (iv) a sensor element mounted proximal to said platform for monitoring an output from the microfluidic device when said device is mounted in or on the platform.

2. An apparatus according to claim 1, further comprising: a microfluidic device mounted in the microfluidic device holding region of the platform said device having a sample input channel fluidly connected to a channel system comprising at least one channel having at least one cross-sectional dimension between about 0.1 $\mu$m and about 500 $\mu$m.

3. An apparatus according to claim 1, further comprising:

(v) an armature configured for moving said platform relative to the plate conveyor system, thereby providing for contact between the at least one microfluidic device and the at least one multiwell plate during operation of the apparatus.

4. An apparatus according to claim 1, further comprising:

(vi) a buffer dispensing system proximal to said plate conveyor system for filling said plurality of multiwell plates.

5. An apparatus according to claim 2, further comprising:

(vii) said microfluidic device mounted in the microfluidic device holding region of the platform and an adapter for mounting a plurality of electrodes in reservoirs of said microfluidic device, which reservoirs are fluidly connected to at least one channel.

6. An apparatus according to claim 1, farther comprising:

(viii) a plurality of multiwell plates in the plate stacking region of the apparatus.

7. An apparatus according to claim 6, wherein said multiwell plates contain said plurality of test compounds.

8. An apparatus according to claim 1, wherein said platform is configured to receive a plurality of microfluidic devices.

9. An apparatus according to claim 2, further comprising: said microfluidic device mounted on said platform wherein said microfluidic device holding region comprises an opening through which a microfluidic channel fluidly connected to said microfluidic substrate contacts a portion of said at least one multiwell plate during operation of the apparatus.

10. An apparatus according to claim 2, wherein said microfluidic device comprises at least one sample input port.

11. An apparatus according to claim 10, wherein said at least one sample input port comprises a pipettor element fluidly coupled to said channel system of said microfluidic device.

12. An apparatus according to claim 1, wherein said conveyor system is a unidirectional conveyor system.

13. An apparatus according to claim 2, wherein said microfluidic device comprises reservoirs in fluid communication with said channel system, said apparatus further comprising an electrokinetic controller comprising a plurality of electrodes which mate with said reservoirs.

14. An apparatus according to claim 11, wherein said sensor element for monitoring said output is a component of an optical detection system.

15. A system for analyzing a plurality of test compounds, said system comprising:

(i) an apparatus for handling a plurality of multiwell plates and at least one microfluidic substrate, the apparatus comprising a multiwell plate movement mechanism for moving said multiwell plates into proximity with said at least one microfluidic substrate, wherein the apparatus moves at least one of the multiwell plates into contact with the at least one microfluidic substrate during operation of the system, wherein said at least one microfluidic substrate comprises a channel system with a channel cross sectional dimension between about 0.1 $\mu$m and about 500 $\mu$m, wherein a signal produced by one or more of said test compounds is monitored by a detector mounted proximal to said microfluidic substrate; and, (ii) a computer to record said signal, said computer comprising: software for controlling fluid flow and direction within said at least one microfluidic, substrate thereby controlling flow of said plurality of test compounds, wherein the computer and the detector are operably connected.

16. A system according to claim 15, said system further comprising: an adapter module, said adapter module providing an interface between said computer and said apparatus.

17. A system according to claim 16, wherein said adapter module connects said computer and said apparatus by at least one of: electrical leads connected to the reservoir based electrodes, a power input, an output from a detection system or a data relay.

18. A system according to claim 15, further comprising: an environmental control system, said environmental control system providing optimum temperature for said system.

19. A system according to claim 15, further comprising: an optical detection system coupled to said channel system of said microfluidic substrate.

20. The apparatus of claim 1, wherein the plate conveyor system is mounted under the platform.

* * * * *

UNITED STATES PATENT AND TRADEMARK OFFICE
CERTIFICATE OF CORRECTION

PATENT NO. : 6,306,659 B1
DATED : October 23, 2001
INVENTOR(S) : Parce et al.

It is certified that error appears in the above-identified patent and that said Letters Patent is hereby corrected as shown below:

<u>Column 36,</u>
Line 8, "11" should be -- 1 --.

Signed and Sealed this

Fourteenth Day of May, 2002

Attest:

JAMES E. ROGAN
*Attesting Officer*     *Director of the United States Patent and Trademark Office*